(12) United States Patent
Kawaura et al.

(10) Patent No.: US 9,017,357 B1
(45) Date of Patent: Apr. 28, 2015

(54) PUNCTURE APPARATUS

(71) Applicant: Terumo Kabushiki Kaisha, Tokyo (JP)

(72) Inventors: Masakatsu Kawaura, Sunnyvale, CA (US); Nao Yokoi, Sunnyvale, CA (US); Yuusuke Takahashi, Hadano (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 14/223,809

(22) Filed: Mar. 24, 2014

(51) Int. Cl.
| | |
|---|---|
| *A61B 17/34* | (2006.01) |
| *A61B 17/42* | (2006.01) |
| *A61B 17/04* | (2006.01) |
| *A61B 17/06* | (2006.01) |
| *A61B 17/062* | (2006.01) |
| *A61B 17/00* | (2006.01) |

(52) U.S. Cl.
CPC .............. *A61B 17/42* (2013.01); *A61B 17/0482* (2013.01); *A61B 17/06109* (2013.01); *A61B 17/062* (2013.01); *A61B 17/3468* (2013.01); *A61B 2017/00805* (2013.01)

(58) Field of Classification Search
USPC ............... 600/29, 37; 606/167, 170–172, 185
See application file for complete search history.

(56) References Cited

U.S. PATENT DOCUMENTS

| | | | |
|---|---|---|---|
| 6,911,003 B2 | 6/2005 | Anderson et al. | |
| 7,131,943 B2 | 11/2006 | Kammerer | |
| 2013/0253531 A1* | 9/2013 | Kawaura et al. | ............... 606/119 |

* cited by examiner

*Primary Examiner* — Ryan Severson
(74) *Attorney, Agent, or Firm* — Buchanan Ingersoll & Rooney PC

(57) ABSTRACT

A puncture apparatus includes a puncture needle for puncturing living body tissue of a living body, and a vaginal-insertion assembly positionable in a vagina of the living body. The vaginal-insertion assembly includes a vaginal-insertion member and an inserter connected to the vaginal-insertion member. The inserter is connected to the vaginal-insertion member so that the distal-most end portion of the inserter is located distally beyond the distal-most end portion of the vaginal-insertion member. The size of distal-most end portion of the inserter is less than the size of the distal-most end portion of the vaginal-insertion member. The vaginal-insertion member and the distal-most end portion of the inserter are movable relative to each other to reduce the distance between the distal-most end of the inserter and the distal-most end of the vaginal-insertion member after inserting the vaginal insertion assembly into the vagina.

20 Claims, 28 Drawing Sheets

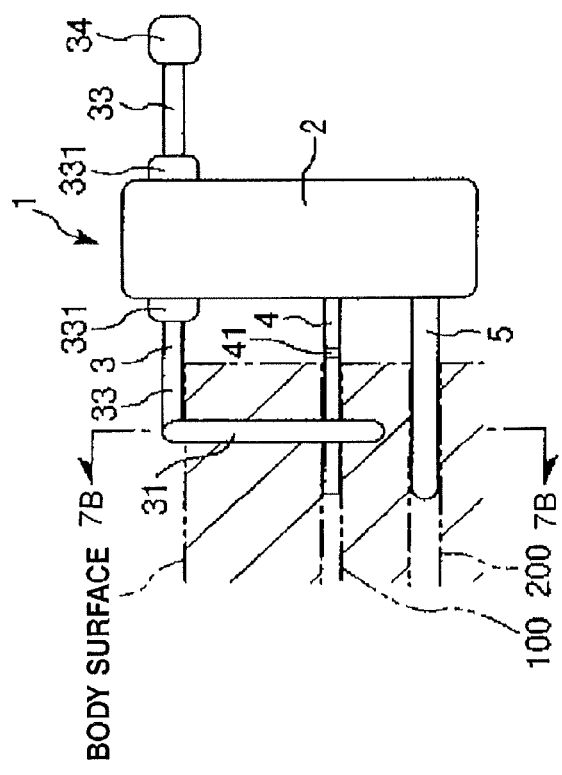
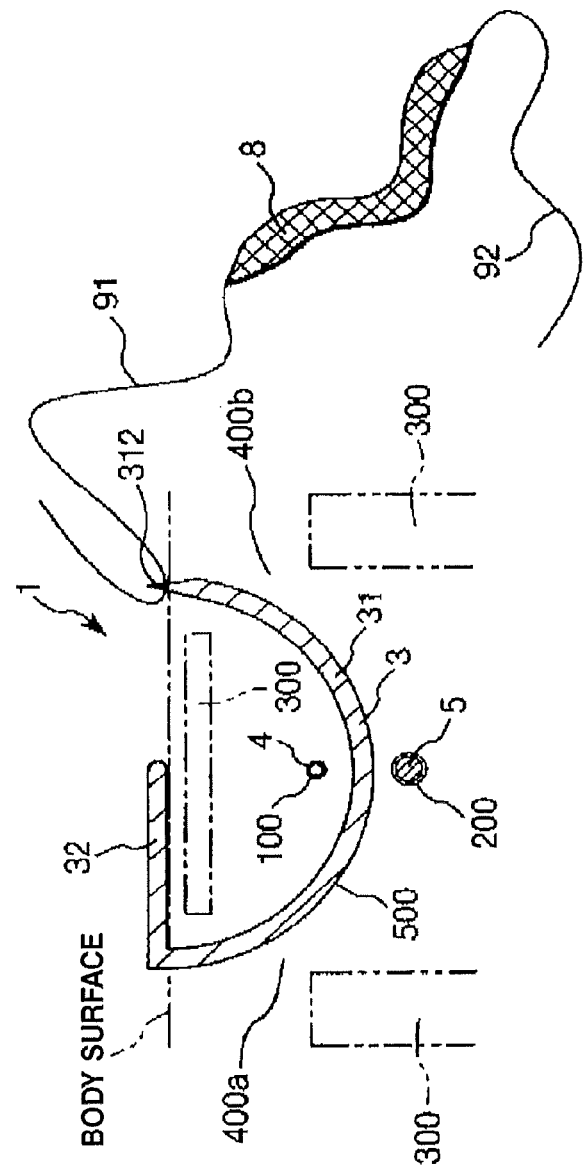
FIG. 7A
FIG. 7B

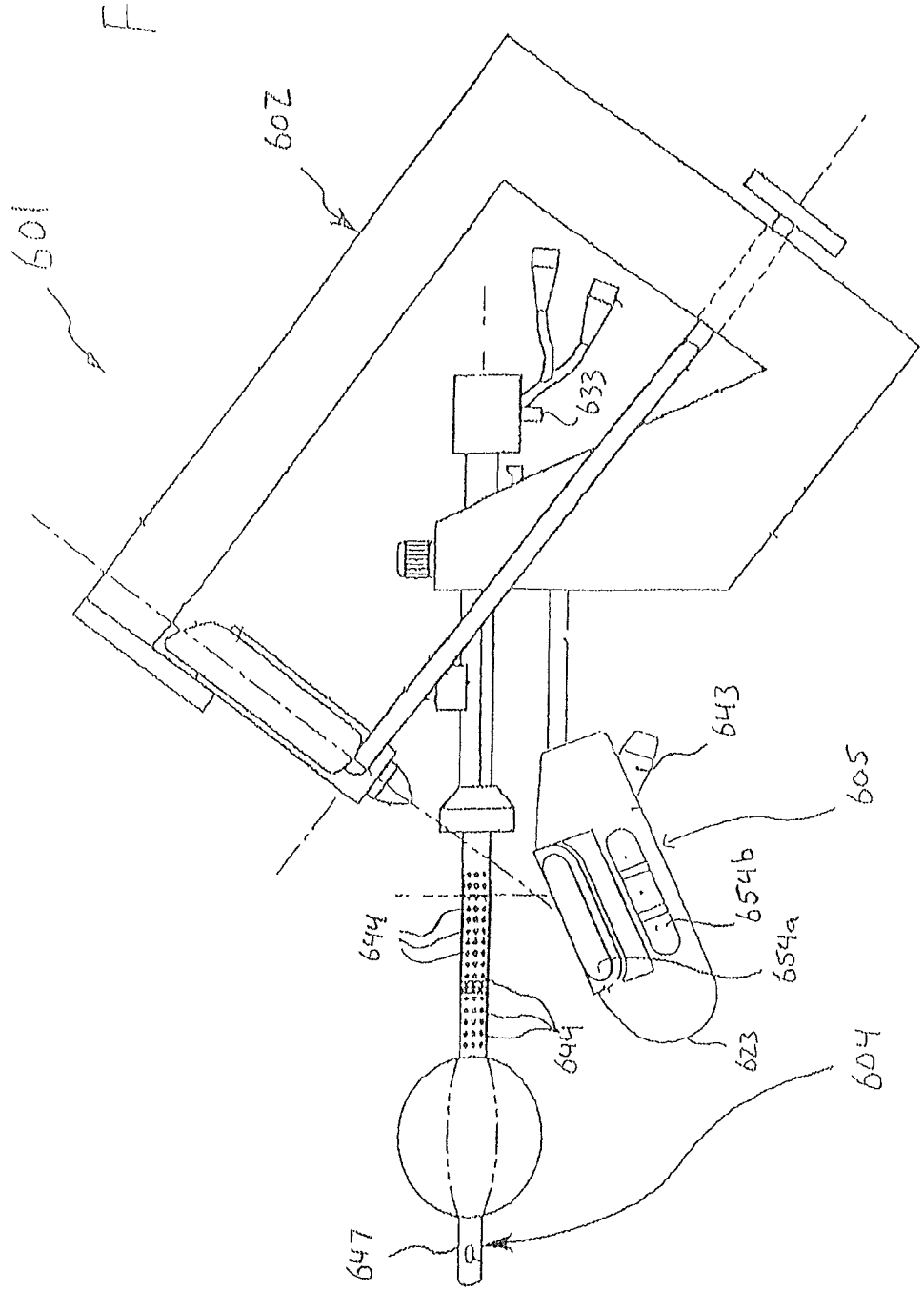

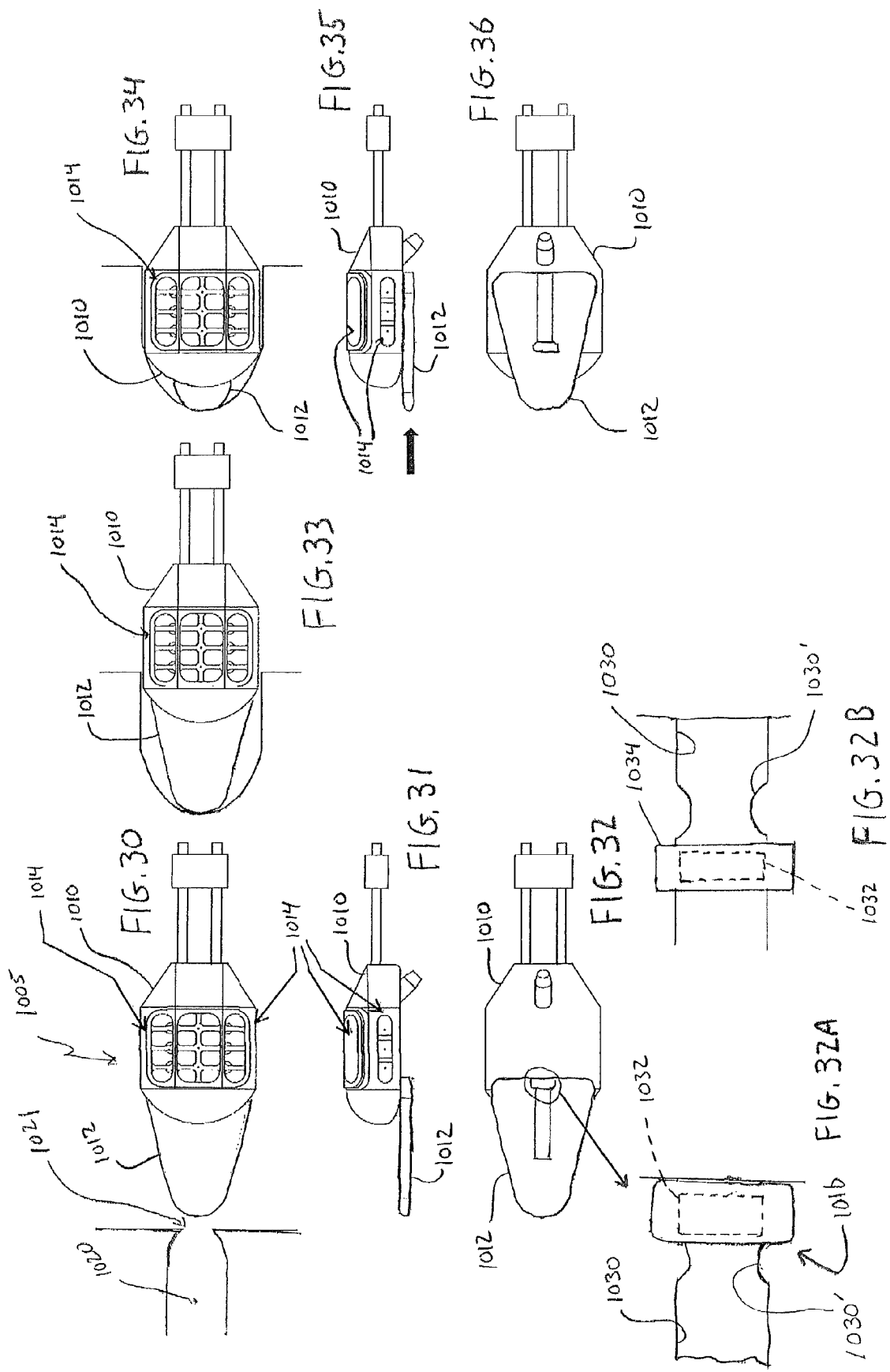

PUNCTURE APPARATUS

CROSS REFERENCES TO RELATED APPLICATIONS

This application contains subject matter disclosed in U.S. Application Publication No. 2013/0253531 published on Sep. 26, 2013, the entire content of which is incorporated herein by reference.

TECHNOLOGICAL FIELD

The present invention generally relates to a puncture apparatus, including an assembly that includes an inserter to facilitate insertion of the assembly into a part of a living body.

BACKGROUND DISCUSSION

When suffering from a urinary incontinence, in particular, when suffering from a stress urinary incontinence, urine leakage occurs caused by the fact that abdominal pressure is applied during a normal exercise or is applied by laughing, coughing, sneezing and the like. For this reason, it is possible to cite, for example, a fact that the pelvic floor muscle which is a muscle for supporting the urethra will loosen caused by a child-bearing or the like.

For the treatment of urinary incontinence, a surgical treatment is effective, in which there is used, for example, a tape-shaped implant referred to as "sling". The "sling" is implanted into the body and the urethra is supported by that sling. An example of this is disclosed in U.S. Pat. No. 6,911,003. In order to indwell the sling inside the body, an operator incises the vagina with a surgical knife, dissects a region between the urethra and the vagina, and communicates that exfoliated region and the outside through an obturator foramen by using a puncture needle or the like. Then, in such a state, the sling is implanted into the body.

However, if the vagina is once incised, there is a fear that there occurs a phenomenon in which the sling will be exposed to the inside of the vagina from a wound caused by the incision thereof, and there is a fear that complications may occur which are caused by an infection from the wound or the like. In addition, since the vagina is incised, the invasiveness of the procedure is rather great and the burden on the patient is large. In addition, there is a fear that the urethra or the like will be damaged in the course of the procedure by the operator, and also, there is a fear that the operator himself will damage his finger tip.

Also, like urinary incontinence, there exists a pelvic organ prolapse as another disorder from which a woman suffers. This disorder is a disorder in which a pelvic organ such as a uterus, a bladder or the like supported in a hammock shape by a pelvic floor muscle group is prolapsed from the vagina caused by the weakening of the pelvic floor muscle group, which can be caused by old age or the like and this is referred to also as a so-called hysterocele or as a cystocele or a rectocele. A repairing method for this pelvic organ prolapse has, in the past, involved a vaginal-wall shortening surgery (colporrhaphy) in which the vaginal wall was incised and the loosened tissue existing between the prolapsed organ and the vaginal wall is partially removed, sutured and shortened. But in recent years, as an alternative technology for that surgery, there has been employed a TVM (Tension-free Vaginal Mesh) surgery and it became possible to prevent the deviation of the pelvic organ from the vagina with lower invasion and also effectively by supporting the prolapsed organ in a hammock shape with a polypropylene-made mesh. An example of this alternative is described in U.S. Pat. No. 7,131,943.

However, like in the treatment of urinary incontinence, when the vagina is incised and the mesh is indwelled, there is a fear that there occurs a phenomenon in which the sling will be exposed to the inside of the vagina from a wound caused by the incision thereof, and there is a fear that there occur complications which are to be caused by an infection from the wound or the like. In addition, since the vagina is incised, the invasiveness of the procedure is rather significant, and the burden on the patient is large. In addition, there is a fear that the urethra or the like will be damaged in the course of the procedure by the operator, and also, there is a fear that the operator himself will damage his finger tip.

SUMMARY

According to one aspect, a puncture apparatus comprises: a supporting member; a puncture member rotatably mounted on the supporting member to rotate about a rotation center; and a vaginal-insertion assembly mounted on the supporting member and positionable in a vagina to assist in properly locating the puncture member. At least a portion of the rotatable puncture member is bent or curved, and the distal end portion of the puncture member constitutes a needle tip which rotates together with the puncture member and is configured to puncture living body tissue as the puncture member is rotated about the rotation center. The vaginal-insertion assembly comprises a vaginal-insertion member and an inserter connected to the vaginal-insertion member. The inserter is connected to the vaginal-insertion member so that the distal-most end portion of the inserter is located distally beyond the distal-most end portion of the vaginal-insertion member such that during insertion of the vaginal-insertion assembly into the vagina the distal-most end portion of the inserter enters the vagina before the distal-most end portion of the vaginal-insertion member enters the vagina. The outer dimension of the distal-most end portion of the inserter is less than the outer dimension of the distal-most end portion of the vaginal-insertion member, and the vaginal-insertion member and the vaginal-insertion member are movable relative to each other to reduce the distance between the distal-most end of the inserter and the distal-most end of the vaginal-insertion member after inserting the vaginal insertion assembly into the vagina so that the vaginal-insertion member is advanced forward into the vagina after the vaginal-insertion assembly is initially positioned in the vagina.

According to another aspect disclosed here, a vaginal-insertion assembly comprises: a vaginal-insertion member possessing a distal-most end portion; and an inserter connected to the vaginal-insertion member and possessing a distal-most end portion. The inserter is connected to the vaginal-insertion member so that the distal-most end portion of the inserter is located distally beyond the distal-most end portion of the vaginal-insertion member such that during insertion of the vaginal-insertion assembly into the vagina the distal-most end portion of the inserter enters the vagina before the distal-most end portion of the vaginal-insertion member enters the vagina. The outer dimension of the distal-most end portion of the inserter is less than the outer dimension of the distal-most end portion of the vaginal-insertion member. The vaginal-insertion member and the distal-most end portion of the inserter are movable relative to each other to reduce the distance between the distal-most end of the inserter and the distal-most end of the vaginal-insertion member after inserting the vaginal insertion assembly into the vagina so that the vaginal-insertion member is advanced forward into the vagina after the vaginal-insertion assembly is initially positioned in the vagina.

Another aspect of the disclosure here involves a method of forming a path in living body tissue. The method involves: inserting a vaginal-insertion assembly into a vagina of a living body, wherein the vaginal-insertion assembly is mounted on a support frame and includes a vaginal-insertion member and an inserter, with the inserter being connected to the vaginal-insertion member. The insertion of the vaginal-insertion assembly into the vagina of the living body includes inserting the distal-most end portion of the inserter into the vagina before inserting the distal-most end portion of the vaginal-insertion member into the vagina, wherein the outer dimension of the distal-most end portion of the inserter is less than the outer dimension of the distal-most end portion of the vaginal-insertion member. The method further includes: relatively moving the vaginal-insertion member and the distal-most end portion of the inserter while the inserter is in the vagina to reduce the distance between the distal-most end of the inserter and the distal-most end of the vaginal-insertion member and forwardly move the vaginal-insertion member into the vagina after the vaginal-insertion assembly; and rotating a puncture member which is mounted on the support frame in a rotational direction about a rotation center while the vaginal-insertion member is positioned in the vagina to puncture tissue of the living body, to move the puncture member along a path of rotational movement passing between the rotation center and the vaginal-insertion assembly, and to exit the living body.

BRIEF DESCRIPTION OF THE DRAWINGS

FIGS. 7A and 7B are views explaining an operating procedure of the puncture apparatus shown in FIG. 1, with FIG. 7B taken along the section line 7B-7B in FIG. 7A.

FIG. 29 is a side view of the puncture apparatus shown in FIG. 28.

FIG. 30 is a top view of one embodiment of a vaginal-insertion assembly disclosed here by way of example and having useful application in, for example, the puncture apparatus illustrated in FIGS. 28 and 29.

FIG. 31 is a side view of the vaginal-insertion assembly shown in FIG. 30.

FIG. 32 is a bottom view of the vaginal-insertion assembly shown in FIG. 30.

FIG. 32A is an enlarged illustration of the circled portion of the vaginal-insertion assembly shown in FIG. 32, and FIG. 32B is an enlarged illustration similar to FIG. 32A illustrating the inserter 1012 moved relative to the vaginal-insertion member 1010.

FIG. 33 is a top view of the vaginal-insertion assembly shown in FIG. 30 illustrating the assembly during initial insertion into a vagina.

FIG. 34 is a top view of the vaginal-insertion assembly shown in FIG. 30 after the assembly is further inserted into the vagina.

FIG. 35 is a side view of the vaginal-insertion assembly shown in FIG. 30 after insertion into the vagina.

FIG. 36 is a bottom view of the vaginal-insertion assembly shown in FIG. 30 after insertion into the vagina.

DETAILED DESCRIPTION

Figure 1:
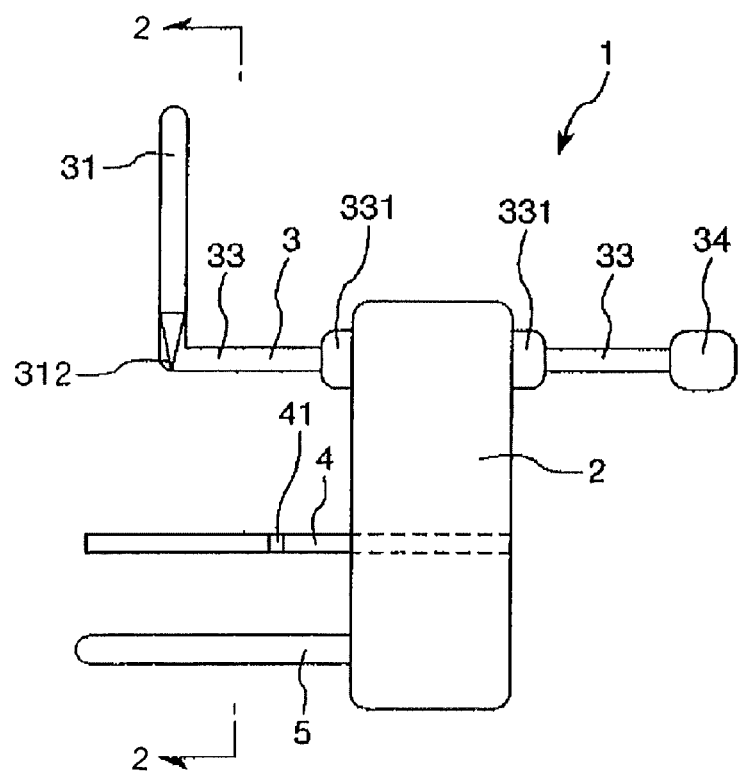
FIG. 1 is a side view of a first embodiment, disclosed by way of example, of a puncture apparatus disclosed here.

FIGS. 1-11 illustrate features and operational aspects of an embodiment of the puncture apparatus disclosed here. In FIG. 4B, FIG. 5B, FIG. 6B, FIG. 7B and FIGS. 8-11, the oblique lines for the living body are omitted so as to be more easily viewable. In the description which follows, the left side in FIG. 1, FIG. 3, FIG. 4A, FIG. 5A, FIG. 6A, FIG. 7A is the "distal end" and the right side is the "proximal end".

The puncture apparatus 1 shown in these drawings is an apparatus to be used for the treatment of woman's urinary incontinence. That is, it is to be used when burying an implant (tool implanted into a living body) for the treatment of urinary incontinence inside the living body.

The implant is a buriable tool for the treatment of woman's urinary incontinence, that is, a tool for supporting the urethra and a tool for supporting the urethra thereof so as to pull it to the direction separated from the vaginal wall when, for example, the urethra is going to move to the vaginal-wall side. For this implant, it is possible to use, for example, a long object having flexibility.

As shown in FIG. 7B, in this embodiment disclosed by way of example, an implant 8 forms an elongated bogy having a mesh-like shape (mesh-shaped) and the overall shape of the implant is a belt-like shape. This implant 8 is referred to as a "sling". It is possible for the implant 8 to be configured as an implant braided in a mesh-like shape (lattice shape), for example, by intersecting line shaped bodies, that is, to be constituted by a braided body having a mesh-like shape. For the line shaped body, examples include a body whose cross-sectional shape is a round shape; whose cross-sectional shape is a flattened shaped, that is, a belt-like shape (ribbon shape); or the like. In addition, at the one end portion of the implant 8, one end portion of a string 91 is fixed and at the other end portion thereof, one end portion of a string 92 is fixed.

Also, there is no limitation in particular for the material forming the implant 8, and it is possible to use, for example, various kinds of resin materials and the like which are biocompatible Also, there is no limitation in particular for the materials forming the strings 91, 92, and it is possible to use, for example, various kinds of resin materials, fibers and the like.

The shape of the implant 8 is not limited to the above-described mesh-like shape.

Figure 2:
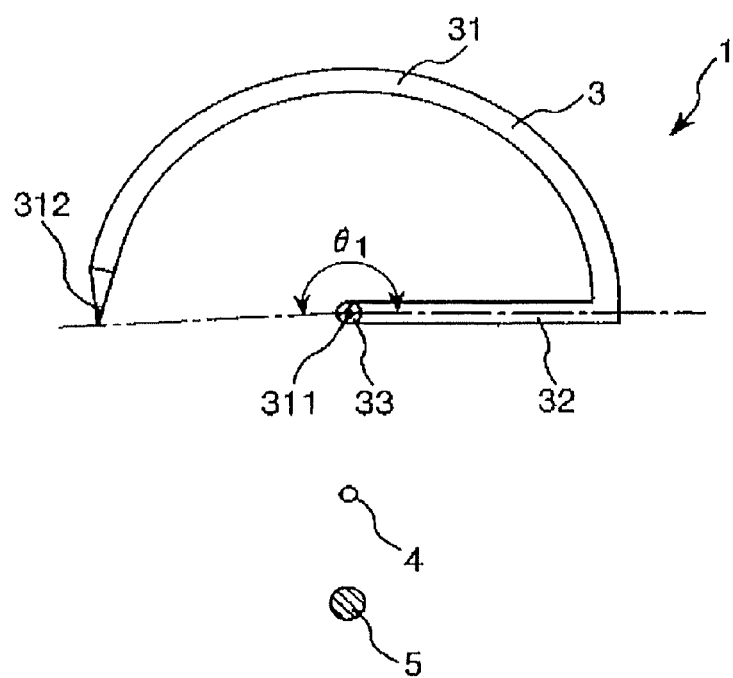
FIG. 2 is a cross-sectional view along the section line 2-2 in FIG. 1.

As shown in FIG. 1 and FIG. 2, the puncture apparatus 1 includes a puncture member 3, a urethral-insertion member 4 possessing an elongated shape and sized and configured to be inserted into a urethra, a vaginal-insertion member 5 possessing an elongated shape and sized and configured to be inserted into a vagina; and a supporting member 2 for supporting the puncture member 3, the urethral-insertion member 4 and the vaginal-insertion member 5. The supporting member 2 is an example of a restriction means for restricting the positional relationship between the puncture member 3 and the urethral-insertion member 4 (and also the vaginal-insertion member 5, if desired), as will be discussed in more detail below. The puncture member 3 includes a puncture needle 31 at a distal end portion of the puncture member for puncturing living body tissue, an axial portion 33 and an interlock portion 32 connecting the puncture needle 31 and the axial portion 33.

Figure 3:
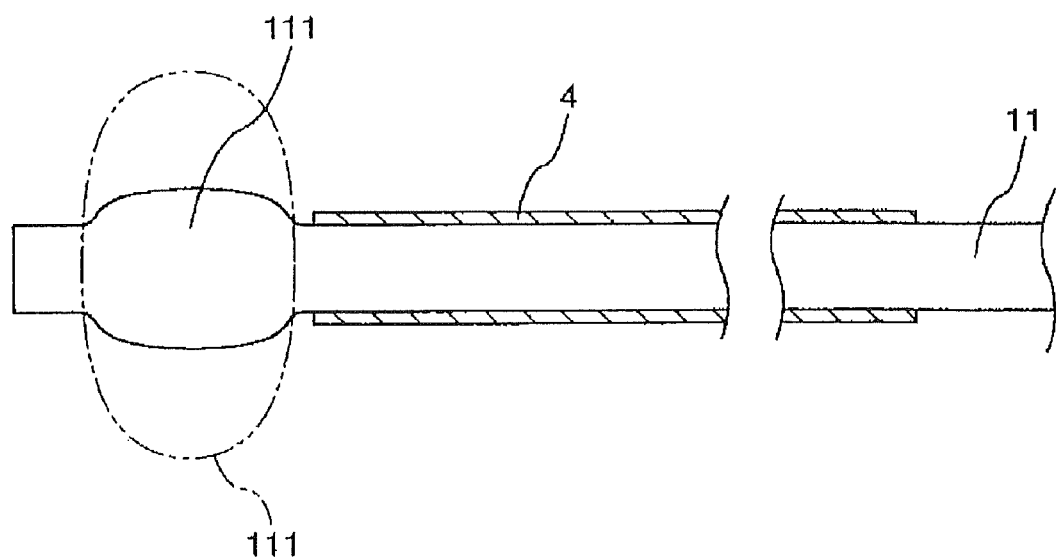
FIG. 3 is a cross-sectional view showing a state in which a balloon catheter is inserted into a urethral-insertion member of the puncture apparatus shown in FIG. 1.

In this embodiment, the urethral-insertion member 4 is firmly-fixed to the supporting member 2. This urethral-insertion member 4 is a straight tubular-shaped body composed of a non-elastic rigid material, and has an opening at the proximal end that opens to the proximal surface of the supporting member 2. It is possible to insert into the inside of the urethral-insertion member 4 various kinds of long-shaped (elongated) medical tools such as, for example, a balloon catheter 11, which is provided with an expandable and contractible balloon 111 at its distal portion such as shown in FIG. 3. In FIG. 3, a state in which the balloon 111 is contracted is indicated by a solid line and a state in which the balloon 111 is expanded is indicated by a two-dot chain line.

The balloon 111 of this balloon catheter 11 functions as a restriction structure for restricting the position of the urethral-insertion member 4 in the axis direction (longitudinal direction) inside the urethra. More specifically, when using the puncture apparatus 1, the balloon 111 is inserted into a bladder of a patient, the positional relation in the axial direction between the balloon catheter 11 and the urethral-insertion member 4 is fixed, and also, by a mechanism in which the balloon 111 is hooked onto the bladder neck in a state of being expanded, the position of the urethral-insertion member 4 with respect to the bladder and the urethra is fixed.

A balloon expanding tool such as, for example, a syringe is connected to a port which communicates with a lumen in communication with the balloon 111 of the balloon catheter 11. The expansion and contraction of the balloon 111 is carried out by feeding an operating fluid supplied by that balloon expanding tool into the inside of the balloon 111 through the mentioned lumen or by pulling out the operating fluid. As the operating fluid for the expansion of the balloon, it is possible to use, for example, a liquid such as a physiological saline or the like, a gas, and the like.

Also, it is possible to use the balloon catheter 11 for the urination of the patient when using the puncture apparatus 1.

A marker 41 is also provided at the outer circumferential portion of the urethral-insertion member 4. This marker 41 is arranged such that the marker 41 is positioned at the urethral opening when the urethral-insertion member 4 is inserted into the urethra and the distal portion of the urethral-insertion member 4 is positioned just before the bladder.

In this embodiment, the vaginal-insertion member 5 is firmly-fixed to the supporting member 2. This vaginal-insertion member 5 is a straight bar shape. Also, the distal portion of the vaginal-insertion member 5 is rounded. Thus, it is possible to insert the vaginal-insertion member 5 smoothly into the vagina.

Also, the vaginal-insertion member 5 is arranged on the lower side of the urethral-insertion member 4 and is separated or spaced from the urethral-insertion member 4 by a predetermined distance such that the axis of the vaginal-insertion member 5 and the axis of the urethral-insertion member 4 are parallel. Preferably at least a proximal portion of the vaginal-insertion member 5 may be parallel with a proximal portion of the urethral-insertion member 4.

There is no limitation in particular for the materials forming the vaginal-insertion member 5, the urethral-insertion member 4 and the supporting member 2. It is possible to use, for example, various kinds of resin materials or the like, or various kinds of metal materials or the like.

With regard to the puncture member 3, the axial portion 33 of the puncture member, also constituting the rotational axis of the puncture member, is placed (mounted) in a freely rotatable manner on the supporting member 2.

Also, the axial portion 33 is arranged on the upper side of the urethral-insertion member 4 and is separated or spaced from the urethral-insertion member 4 by a predetermined distance such that the axis of the axial portion 33 and the axis of the urethral-insertion member 4 are parallel. Also, when seen from the axial direction of the axial portion 33, the axial portion 33, the urethral-insertion member 4 and the vaginal-insertion member 5 are arranged on a straight line. The axis of the axial portion 33 exists in the same plane (plane surface) as that of the axis of the urethral-insertion member 4. The axis of the axial portion 33 also exists on the same plane (plane surface) same as that of the axis of the vaginal insertion member 5. Thus, as seen in FIG. 2, the axis of the axial portion 33, the axis of the urethral-insertion member 4, and the axis of the vaginal insertion member 5 lie in a common plane (a plane perpendicular to the plane of the paper).

This axial portion 33 passes completely through the supporting member 2 in the right and left direction in FIG. 1. On the distal side and the proximal side of the axial portion 33, there are formed a flange 331 and a flange 332 respectively through the supporting member 2, and depending on these flanges 331, 332, the movement toward the axis direction of the axial portion 33 with respect to the supporting member 2 is blocked.

The distal end of the puncture needle 31 has a sharp needle tip, and the puncture needle 31 bends in an arc shape centered on the axial portion 33. Also, in FIG. 1, the axis of the puncture needle 31 and the axis of the axial portion 33 are orthogonal. Thus, when the puncture member 3 is moved rotationally, the needle tip of the puncture needle 31 moves along the arc in a surface perpendicular to the axis of the axial portion 33 and more specifically, moves in a surface in which the aforesaid axis is a normal line.

The puncture needle 31 moves along a predetermined orbit. It is possible for the needle tip of the puncture needle 31 to move by drawing a preliminarily defined arc-shaped orbit centered on the axial portion 33. The orbit of the puncture needle 31 passes a far-position side compared with the urethral-insertion member 4. The orbit of the puncture needle 31 passes a portion between the urethral-insertion member 4 and vaginal-insertion member 5.

There is no problem even if the distal end of the puncture needle 31 has an obtuse needle tip of such a degree in which there is no obstacle to progress toward the inside of the living body tissue. It is possible to employ another or different member for the needle tip of the puncture needle 31.

Also, in this embodiment disclosed by way of example, the needle tip of the puncture needle 31 is directed toward the counterclockwise direction in FIG. 2, but it is not limited to this configuration as it is also possible for the needle to be directed toward the clockwise direction in FIG. 2.

It is also possible for the puncture needle 31 to be solid and it is also possible for the needle to have a tubular and hollow shape.

Also, in this embodiment, the puncture needle 31 is arranged on the proximal side relative to the distal portion (distal-most end) of the urethral-insertion member 4 in the axial direction of the urethral-insertion member 4.

It is also possible however for the puncture needle 31 to be arranged at the same position as the distal portion (distal-most end) of the urethral-insertion member 4 in the axial direction of the urethral-insertion member 4. Additionally, the needle 32 can be arranged on the distal side of the distal portion (distal-most end) of the urethral-insertion member 4.

Here, the supporting member 2 restricts the positional relation between the puncture member 3 and the urethral-insertion member 4 such that when the puncture member 3 moves rotationally (rotates) and punctures the living body tissue, the needle tip of the puncture needle 31 passes, relative to the urethral-insertion member 4 or an extended line (imaginary continuation) of such member, a far-position side from the center 311 of the puncture needle 31 so that is passes to a lower side of the urethral-insertion member 4 or an extended line of such member. That is, during rotation of the needle 31, the tip of the needle passes on the side (lower side in FIG. 2) of the urethral-insertion member 4 that is opposite the rotation center 33 of the needle such that the urethral-insertion member 4 is positioned between the center 33 and the lower portion of the path of movement of the needle tip. The center 311 of the puncture needle 31 is the center of the arc in the puncture needle 31, that is, is the rotary center of the puncture needle 31 (puncture member 3).

The positional relationship between the puncture member 3 and the urethral-insertion member 4 is fixed such that the orbit of the needle tip of the puncture member 3 does not intersect the urethral-insertion member 4 or the extended line thereof and such that the orbit of the needle tip of the puncture needle 31 will pass the lower side of the urethral-insertion member 4 or the extended line (imaginary extension) of such line.

With regard to the positional relation between the orbit of the needle tip of the puncture member 3 and the urethral-insertion member 4, other than the configuration in which the position is maintain by such a member as the aforementioned supporting member 2, it is possible to employ a guide member which is connected with the urethral-insertion member 4 and which is insertable into the urethral-insertion member 4 such that the puncture member 3 makes a movement by a certain orbit. Also, it is possible to employ a configuration in which the urethral-insertion member 4 and the puncture member 3 are connected directly and the puncture member 3 is configured to make a movement by a certain orbit, whereby the positional relation is fixed such that the orbit of the needle tip of the puncture needle 31 will pass the lower side of the urethral-insertion member 4 or the extended line thereof.

Also, it is possible for the urethral-insertion member 4 to be provided with a marker which is visually recognizable under the noninvasive monitoring of the inside of the body by X-ray, ultrasound or the like. While confirming the position of the urethral-insertion member 4 by a monitor while emitting the X-ray or the ultrasound, it is possible to pass the needle tip through a desired position by setting a condition in which the orbit of the needle tip of the puncture needle 31 will surely pass the lower side of the urethra and by executing the puncture. Further, it is possible for the vaginal insertion member 5 to be provided with a similar marker. It is possible to employ a configuration in which the orbit of the needle tip of the puncture needle 31 is displayed on the monitor such that the position of the urethral-insertion member 4 and the position of the orbit can be confirmed on the monitor. In a case in which the position of the urethral-insertion member 4 and the position of the orbit on the monitor intersect each other, a mechanism can be provided which can move the puncture member 3 automatically or manually such that the position of the orbit does not overlap. When employing such an embodiment, the positional relation between the orbit of the needle tip of the puncture needle 31 and the urethral-insertion member 4 can be maintained by a series of systems including the mechanism mentioned above.

Further, the supporting member 2 restricts the positional relation between the puncture member 3 and the vaginal-insertion member 5 such that when the puncture member 3 moves rotationally and punctures the living body tissue, the needle tip of the puncture needle 31 does not interfere with the vaginal-insertion member 5 and the extended line thereof.

More specifically, the supporting member 2 restricts the positional relation between the puncture member 3, the urethral-insertion member 4 and the vaginal-insertion member 5 such that when the puncture member 3 rotates or moves rotationally and punctures the living body tissue, the needle tip of the puncture needle 31 passes a position between the urethral-insertion member 4 or the extended line thereof and the vaginal-insertion member 5 or the extended line thereof.

Thus, depending on the puncture needle 31, it is possible to puncture the living body tissue by avoiding the urethra and the vaginal wall, and it is possible to prevent a phenomenon in which the puncture needle 31 will puncture the urethra and will puncture the vaginal wall.

Also, the orbit of the needle tip of the puncture needle 31 is determined so that it is possible for the operator himself to prevent a phenomenon of puncturing his finger tip by the puncture needle 31. Safety can thus be obtained.

There is no limitation in particular for the center angle $\theta 1$ of the arc of the puncture needle 31. This angle is an angle to be set arbitrarily in response to various conditions, and this angle is set such that when puncturing living body tissue by the puncture needle 31, it becomes possible for the puncture needle 31 to enter into the body from one body surface of the patient, to pass the lower side of the urethra and to protrude to the body outside from the other body surface.

Specifically, it is preferable for the center angle $\theta 1$ of the arc of the puncture needle 31 to be 150° to 270°, more preferably 170° to 250° or less, and still more preferably 190° to 230°.

Thus, when puncturing living body tissue by the puncture needle 31, it is possible for the puncture needle 31 to reliably enter into the body from one body surface of the patient, to pass the lower side of the urethra and to protrude to the body outside from the other body surface.

Also, at the distal portion of the puncture needle 31, there is formed a through-hole 312. This through-hole 312 passes through the puncture needle 31 toward the direction which is perpendicular with respect to the axis of the puncture needle 31. Also, either one of the strings 91, 92 which are fixed to the aforementioned implant 8 is inserted into this through-hole 312 and is detachably held (see FIG. 7B).

Also, at the proximal portion of the axial portion 33, there is provided a grasping unit 34 as an operation unit for operating the puncture member 3 rotationally. In this embodiment disclosed by way of example, this grasping unit 34 is in the shape of a rectangular solid. When moving the puncture member 3 rotationally, the grasping unit 34 is grasped by hand and fingers, and is moved rotationally toward a predetermined direction. Needless to say, the shape of the grasping unit 34 is not limited by the illustrated and described configuration.

There is no limitation in particular for the material forming the puncture member 3 and it is possible to use various kinds of rigid materials, such as metal materials, such as metal materials and resin materials. Examples of metal materials include stainless steel, aluminum or aluminum alloy and titanium or titanium alloy, or the like, and examples of resin materials include polyimide or polyamide, or the like. Puncture member 3 may include an outer elongate tube and an inner solid shaft.

Set forth next is a description of an operating procedure using the puncture apparatus 1, that is, a procedure when burying the implant 8 inside the living body.

Initially, there will be explained a method of forming a path for burying the implant 8 inside the living body.

Figure 4A:
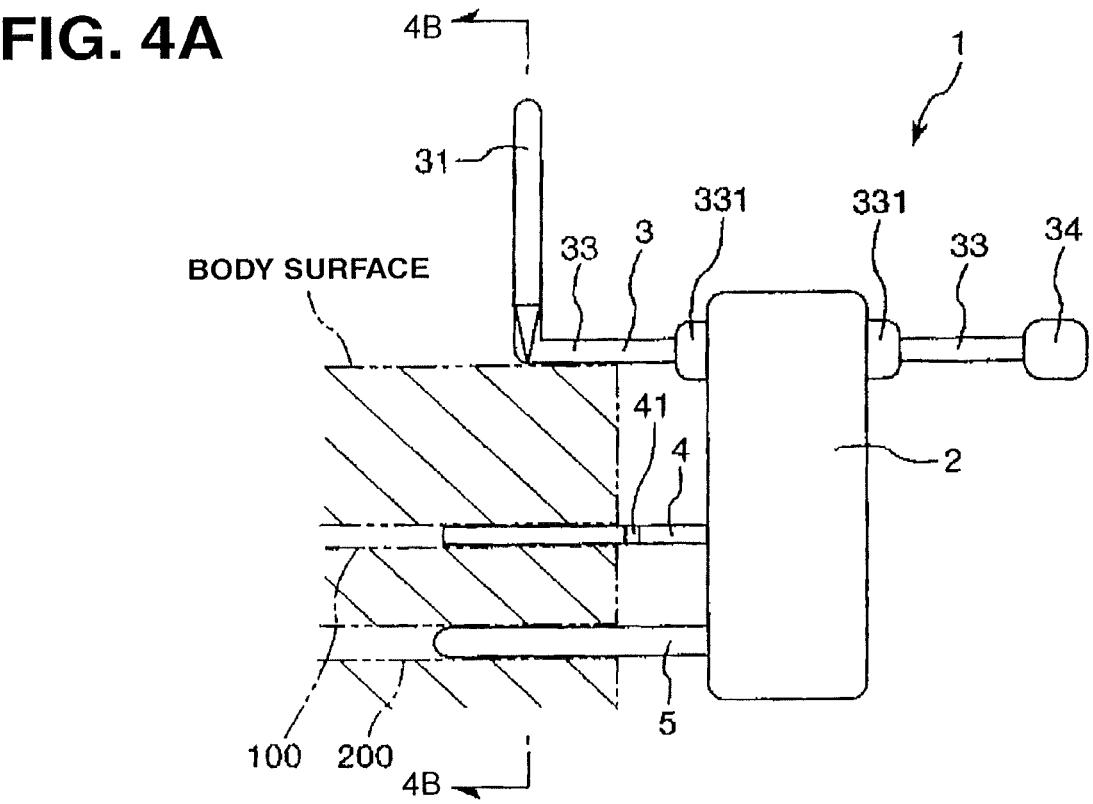
FIGS. 4A and 4B are views explaining an operating procedure of the puncture apparatus shown in FIG. 1, with FIG. 4B taken along the section line 4B-4B in FIG. 4A.
Figure 4B:
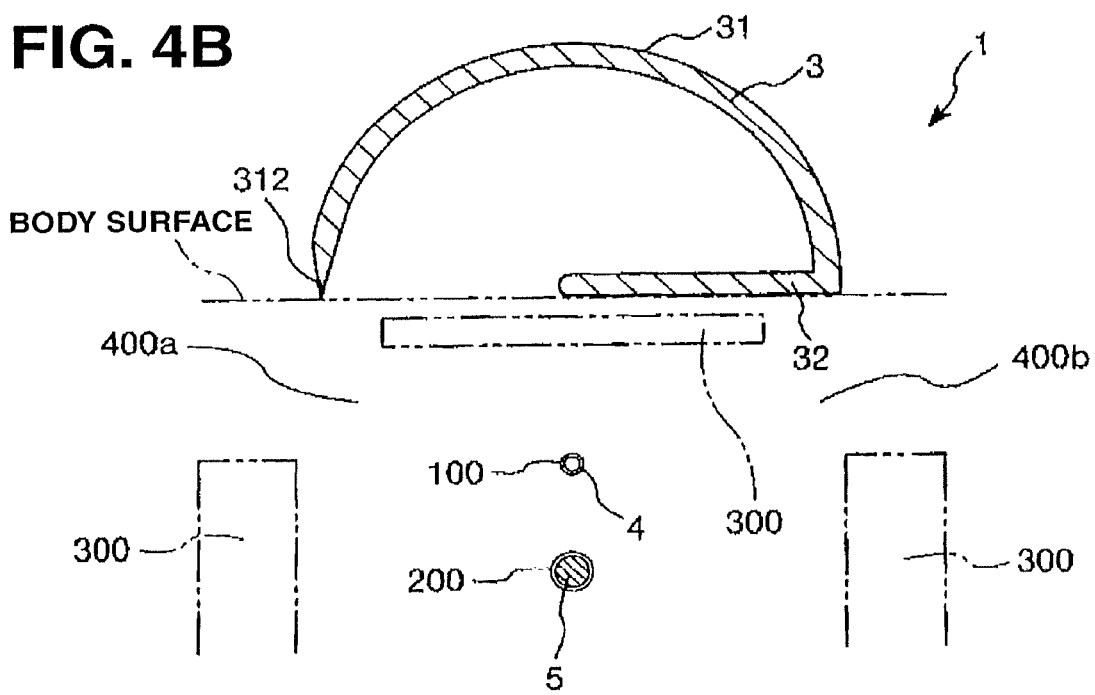

First, as shown in FIGS. 4A and 4B, the puncture apparatus 1 is attached to a patient. More specifically, the urethral-insertion member 4 of the puncture apparatus 1 is inserted into a urethra 100 of the patient and concurrently, the vaginal-insertion member 5 is inserted into a vagina 200 of the patient. At that time, the insertion is carried out such that the marker 41 will be positioned at the urethral orifice or on the front side of the urethral orifice. Thus, it is possible to arrange the distal portion of the urethral-insertion member 4 on the front side of the bladder.

Figure 5A:
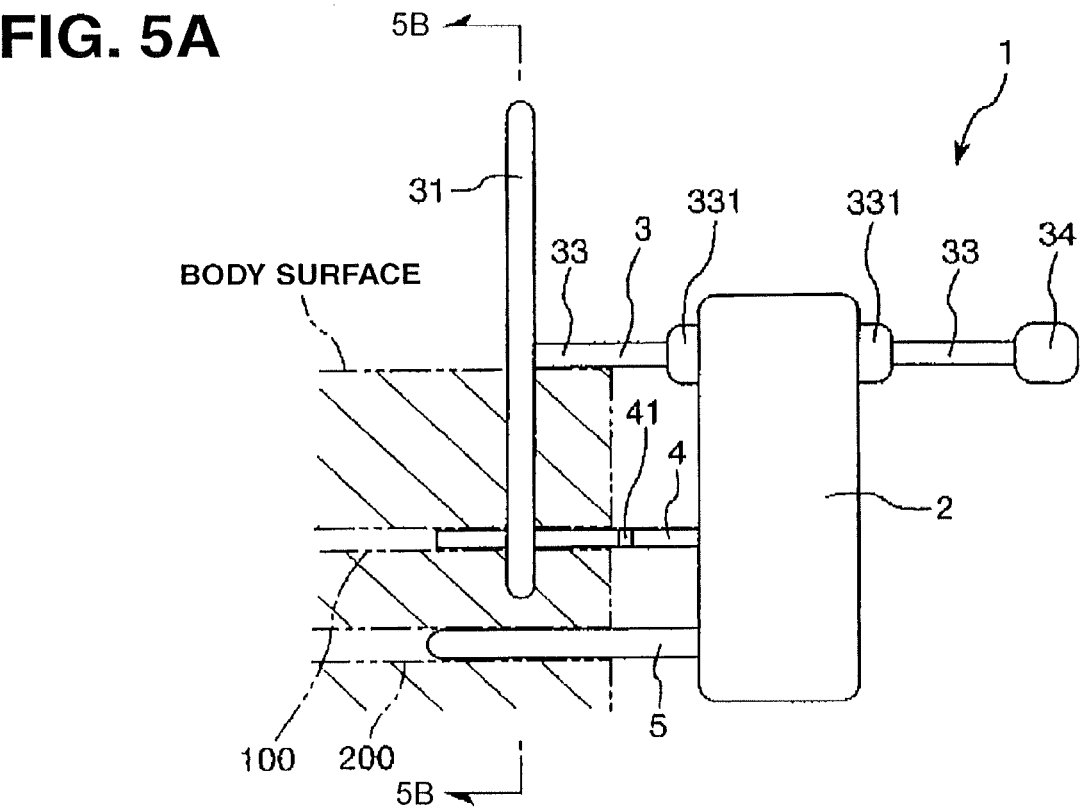
FIGS. 5A and 5B are views explaining an operating procedure of the puncture apparatus shown in FIG. 1, with FIG. 5B taken along the section line 5B-5B in FIG. 5A.
Figure 5B:
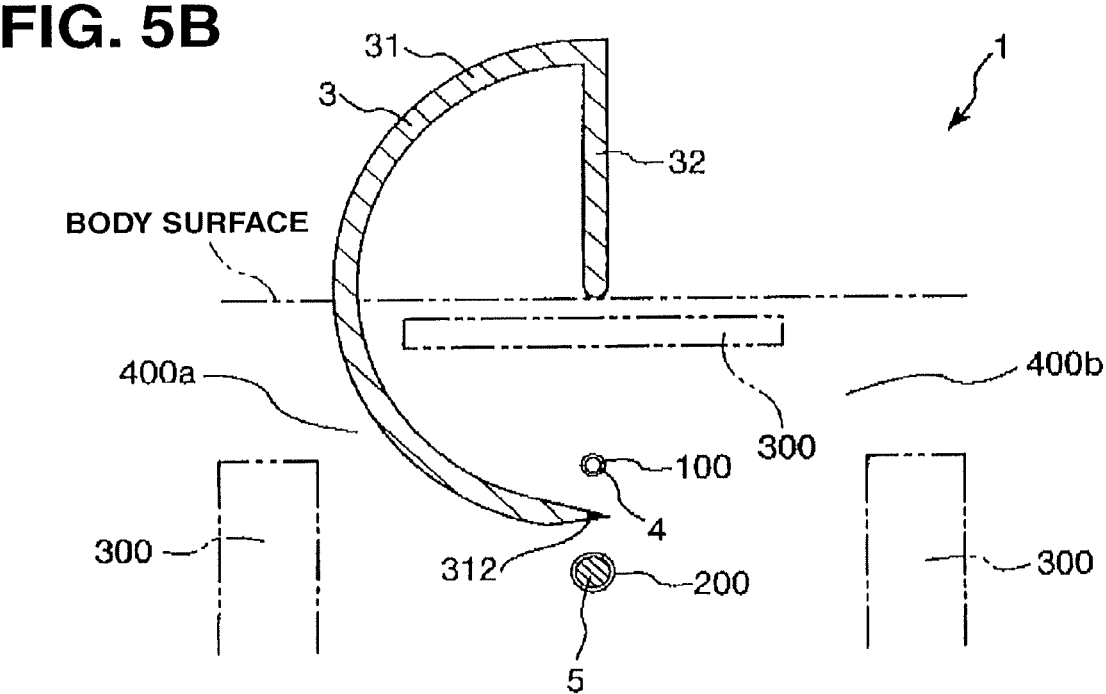
Figure 6A:
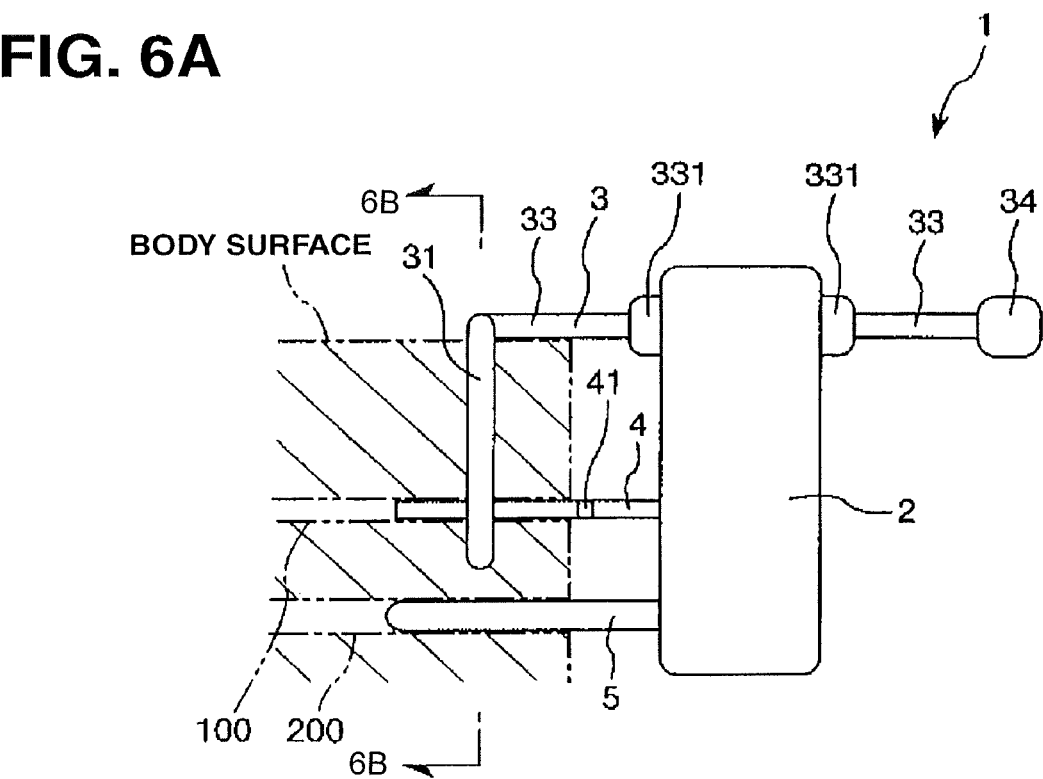
FIGS. 6A and 6B are views explaining an operating procedure of the puncture apparatus shown in FIG. 1, with FIG. 6B taken along the section line 6B-6B in FIG. 6A.
Figure 6B:
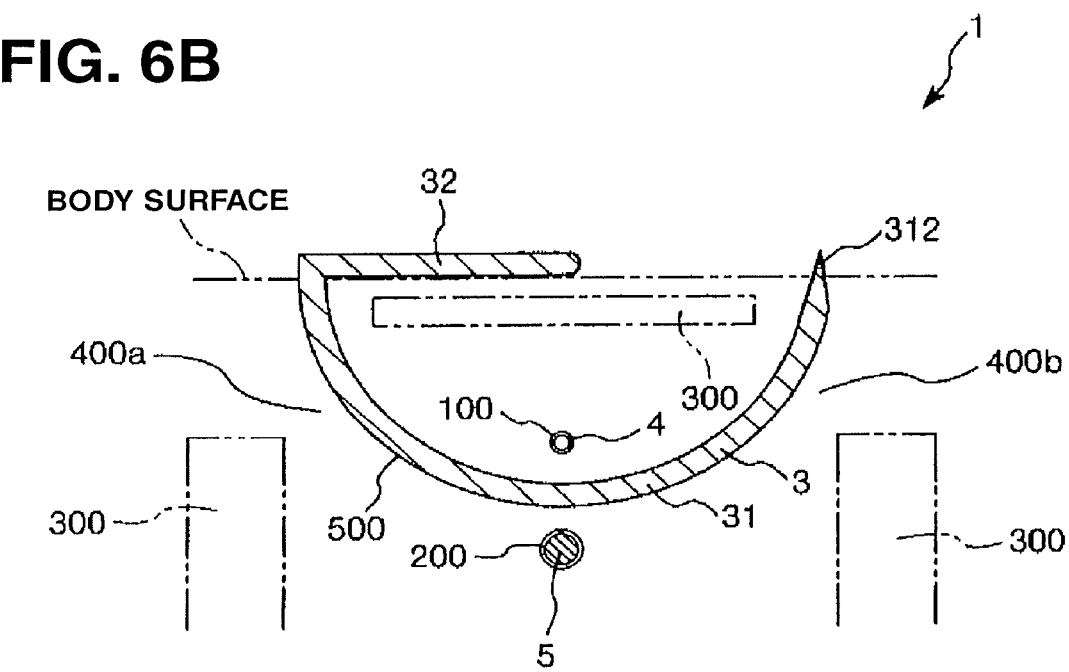

Next, as shown in FIGS. 5A, 5B, 6A and 6B, the grasping unit 34 is grasped and the puncture member 3 is rotated counterclockwise in FIG. 5B and FIG. 6B.

Thus, the member 3 percutaneously moves into a tissue of the body. First the needle tip of the puncture needle 31 moves counterclockwise in FIG. 5B and FIG. 6B along the arc of the needle; punctures the body surface at an interlock region of the patient on the left side in FIG. 5B and FIG. 6B or at a region in the vicinity of such region; enters into the body; passes an obturator foramen 400a of a pelvis 300; passes the lower side of the urethra 100, that is, passes between the urethra 100 and the vagina 200; passes an obturator foramen 400b of the pelvis 300; and protrudes back outside the body be exiting the body surface at an interlock region on the right side in FIG. 5B and FIG. 6B or at a region in the vicinity of such region. Thus, for the patient, there is formed a through-hole 500 which starts from the body surface at an interlock region on the left side in FIG. 5B and FIG. 6B or at a region in the vicinity of such region and which reaches the body surface at an interlock region on the right side in FIG. 5B and FIG. 6B or at a region in the vicinity of such region by passing through the obturator foramen 400a, the space between the urethra 100 and the vagina 200 and the obturator foramen 400b.

The through-hole 500 maintains a non-opened state with respect to the urethra 100 and the vagina 200. It is preferable for the orbit of the needle tip of the puncture needle 31 to pass a region on the inner side (near the pubic-bone connection) from the center of the obturator foramen 400b of the pelvis 300. It is more preferable for the orbit to pass a region referred to as a so-called safety zone (or safety-entry zone) within the regions near the pubic-bone connection from the center of the obturator foramen 400b. This is because there are few nerves or blood vessels in such regions, for which injuries are desired to be avoided, and because it is possible to carry out the puncture safely.

There will next be explained a procedure of passing an implant through the path and indwelling the implant.

As shown in FIGS. 7A and 7B, the end portion of either one of the strings 91, 92 fixed to the implant 8 is inserted through the through-hole 312 of the puncture needle 31, there is inserted the end portion of either one of the strings 91, 92 fixed to the implant 8. In the illustrated example, the end portion of string 91 is inserted through the through-hole 312 of the puncture needle 31. Thus, the end portion of the string 91 is held at the distal portion of the puncture needle 31.

Figure 8:
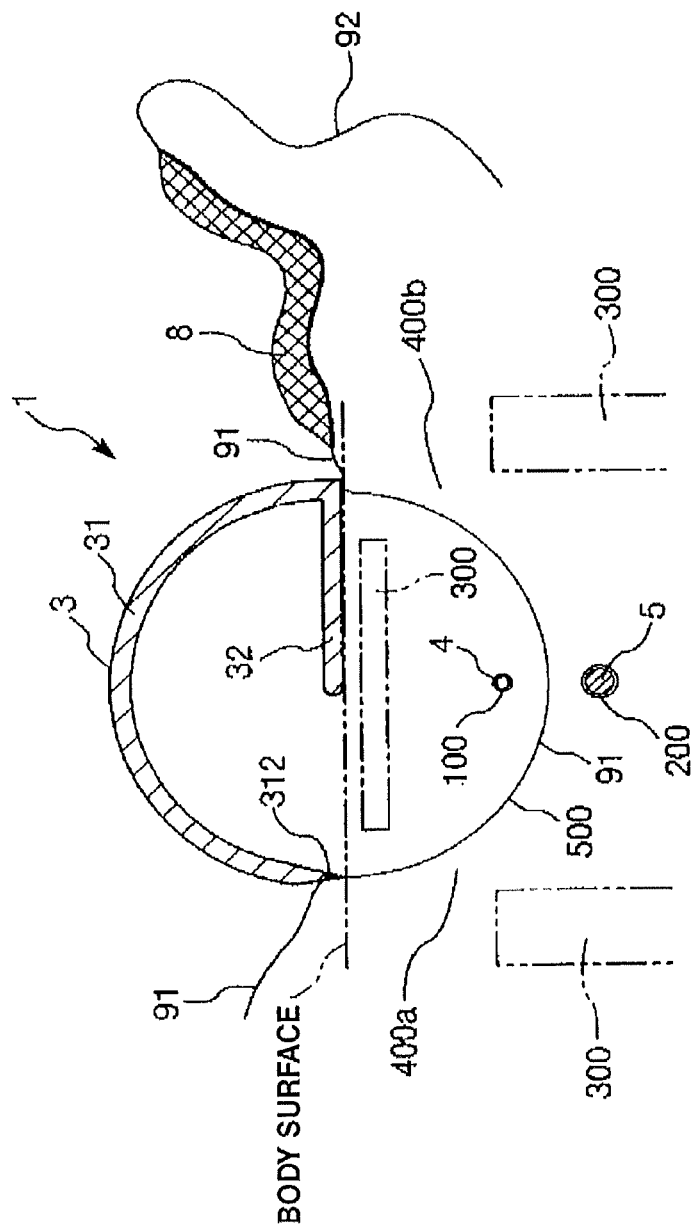
FIG. 8 is a cross-sectional view explaining an operating procedure of the puncture apparatus shown in FIG. 1.

Next, as shown in FIG. 8, the grasping unit 34 is grasped and the puncture member 3 is rotated clockwise in FIG. 8.

Thus, the needle tip of the puncture needle 31 moves clockwise in FIG. 8 along an arc; enters the body from the interlock region of the patient on the right side in FIG. 8 or from a body surface in a region in the vicinity of such region; passes the obturator foramen 400*b* of the pelvis 300; passes the lower side of the urethra 100, that is, passes between the urethra 100 and the vagina 200; passes the obturator foramen 400*a* of the pelvis 300; and exits to the outside of the body from the interlock region on the left side in FIG. 8 or from a body surface in a region in the vicinity of such region. More specifically, the puncture needle 31 is pulled out or moved to the outside of the body.

Figure 9:
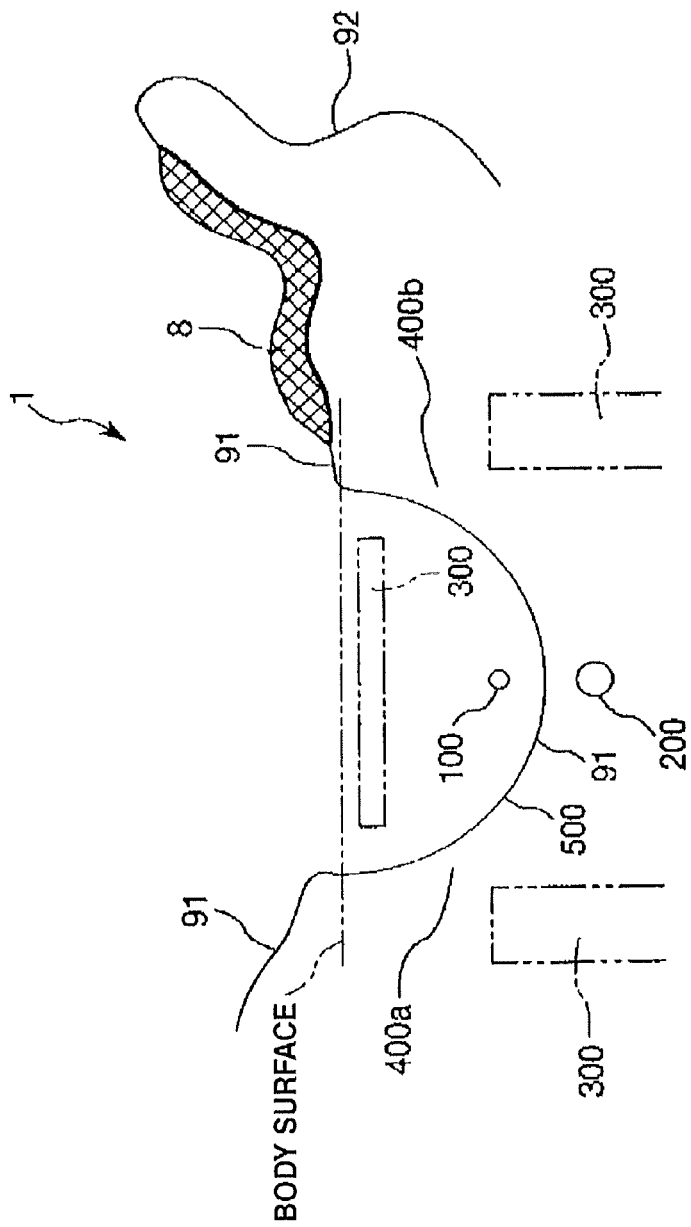
FIG. 9 is a cross-sectional view explaining an operating procedure of the puncture apparatus shown in FIG. 1.

Next, as shown in FIG. 9, the end portion of the string 91 is pulled out from the through-hole 312 of the puncture needle 31. Also, the puncture apparatus 1 is removed from the patient. More specifically, the urethral-insertion member 4 is pulled out from the inside of the urethra 100 and concurrently, the vaginal-insertion member 5 is pulled out from the inside of the vagina 200 of the patient.

Figure 10:
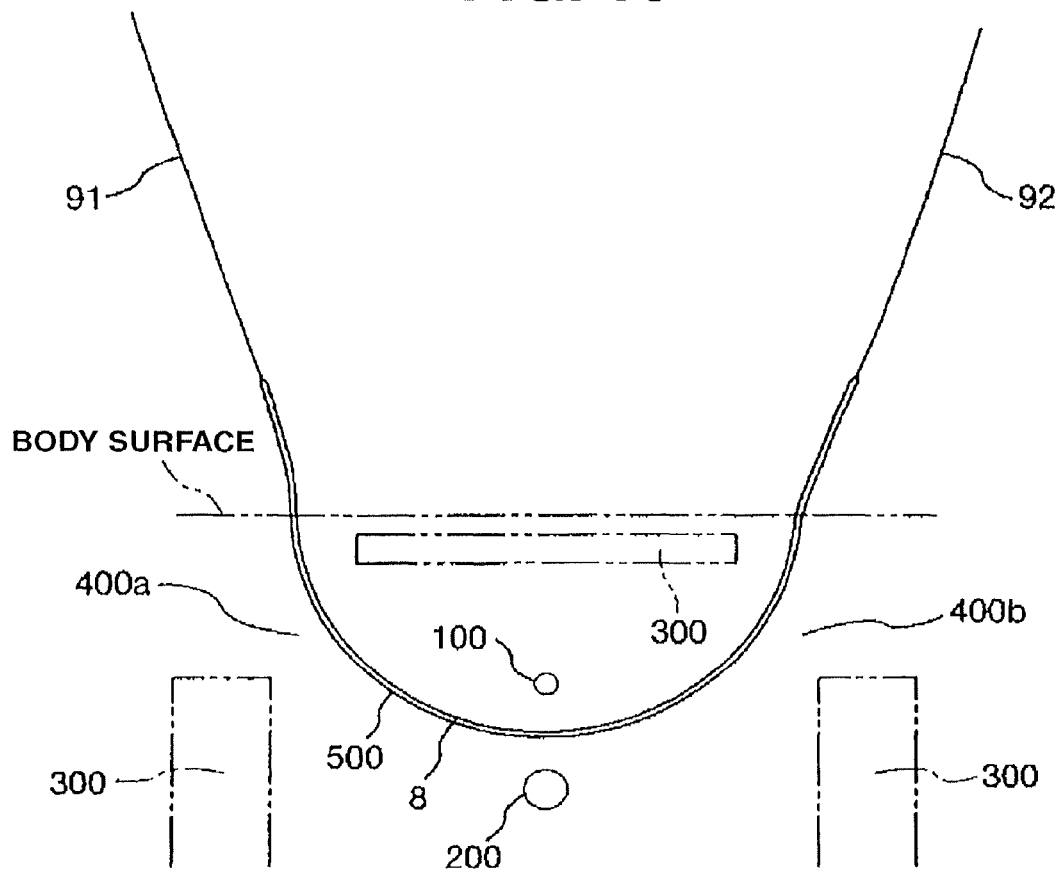
FIG. 10 is a cross-sectional view explaining an operating procedure of the puncture apparatus shown in FIG. 1.

Next, as shown in FIG. 10, the string 91 is pulled while pulling the string 92, the implant 8 is inserted into the through-hole 500 which is formed in the patient; and while the end portion of the implant 8 on the right side in FIG. 10 is remained on the outside of the body, the end portion of the implant 8 on the left side in FIG. 10 is pulled out from the through-hole 500 to the outside of the body.

Figure 11:
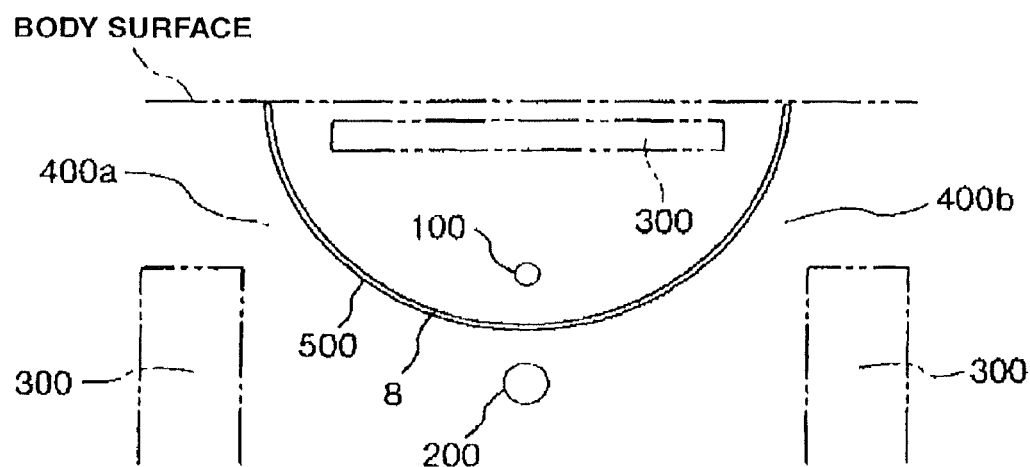
FIG. 11 is a cross-sectional view explaining an operating procedure of the puncture apparatus shown in FIG. 1.

Next, as shown in FIG. 11, the strings 91, 92 are pulled respectively by predetermined forces, the position of the implant 8 with respect to the urethra 100 is adjusted, unnecessary portions of the implant 8 are cut out, and afterward the procedure is completed.

As explained above, according to this puncture apparatus 1, when indwelling an implant, it is possible to make a correspondence only by a procedure exhibiting relatively low invasiveness, involving a puncture of the puncture needle 31 or the like, and it is not necessary to carry out a highly invasive incision or the like, so that the burden on the patient is relatively small and also, the safety of the patient is quite high.

Also, because the living body can be punctured by the puncture needle 31 by avoiding the urethra and the vaginal wall, it is possible to prevent a phenomenon in which the puncture needle 31 will puncture the urethra and will puncture the vaginal wall, thus facilitating a safe result. Also, it is possible for the operator himself to prevent a phenomenon in which his finger tip will be punctured by the puncture needle 31 and so safety can be obtained.

Also, it is possible to prevent a phenomenon in which, such as in a conventional case of incising a vagina, the implant is exposed to the inside of the vagina from a wound caused by the incision and in which complications occur which are caused by an infection from the wound or the like.

In this embodiment disclosed by way of example, the puncture hole formed for the patient by the puncture needle 31 is a through-hole, but it is not limited by this configuration and it is possible for the puncture hole not to employ a passing-through type.

Also, the urethral-insertion member is not limited to a tubular-shaped member and it is possible, for example, to employ a solid member, and in addition, it is also possible to employ a member which is hollow and in which either one or both of the distal portion and the proximal portion of the hollow member are occluded.

The distal portion of the urethral-insertion member can be provided with an expandable a contractible balloon as a restriction structure for restricting the position in the axial direction of the urethral-insertion member inside the urethra.

Also, in this embodiment, the puncture needle of the puncture member is a needle, the whole of which is bent in an arc shape. But the needle is not limited to this shape or configuration, and it is possible, for example, to employ a needle including a region bent in an arc shape only for a portion of the length of the needle. More specifically, it is enough if the puncture needle includes a region bent in an arc shape at least for a portion of the extent of the needle.

Also, it is sufficient if the puncture needle of the puncture member includes a bent region at least for a portion of its length and it is possible, for example, to employ a needle, the whole of which is bent in an elliptical arc shape and to employ a needle which includes a region bent in an elliptical arc shape only for a portion of its length. More specifically, it is possible for the puncture needle to include a region bent in an elliptical arc shape at least for a portion of its extent.

Figure 19A:
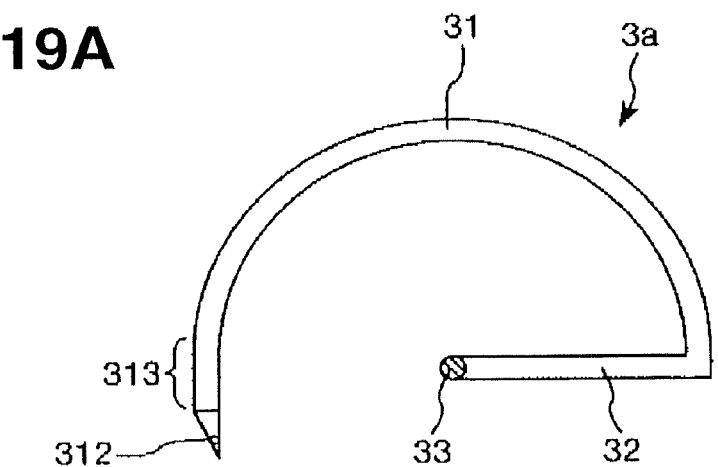
FIGS. 19A to 19C are cross-sectional views showing another example of the puncture member disclosed here.

Set forth next is a description of other examples of the puncture member disclosed here. The puncture needle 31 of the puncture member 3*a* shown in FIG. 19A includes a linear shaped portion 313 forming a linear shape at the distal portion of the needle. This linear-shaped portion 313 protrudes in the direction of a tangent line of the end portion of the needle from the end portion on the distal side of the arc of the puncture needle 31.

In case of using this puncture member 3*a*, before rotating the puncture member 3*a*, the puncture member 3*a* is first pressed against the patient and the linear shaped portion 313 of the puncture needle 31 punctures the patient.

Figure 19B:
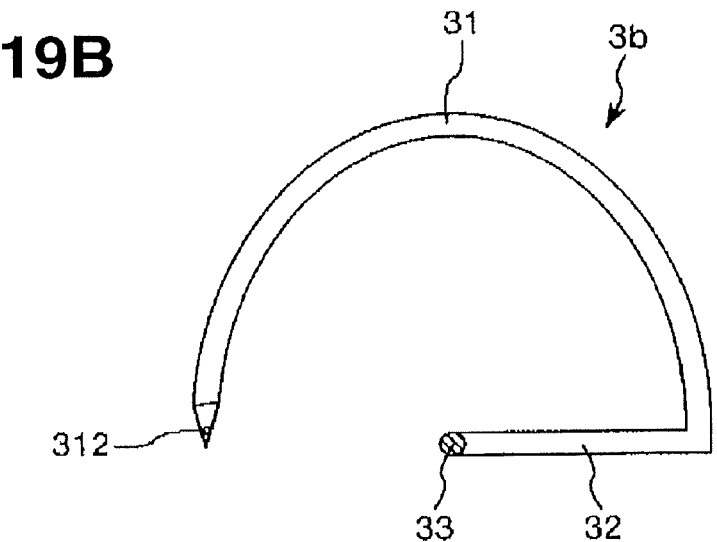

The puncture needle 31 of the puncture member 3*b* shown in FIG. 19B is bent in an elliptical arc shape centered on the axial portion 33. The long axis direction of the ellipse coincides with the up and down direction in FIG. 19B.

It is possible to use this puncture member 3*b* preferably in a case in which the urethra of the patient is positioned at a deep place from her body surface.

Figure 19C:
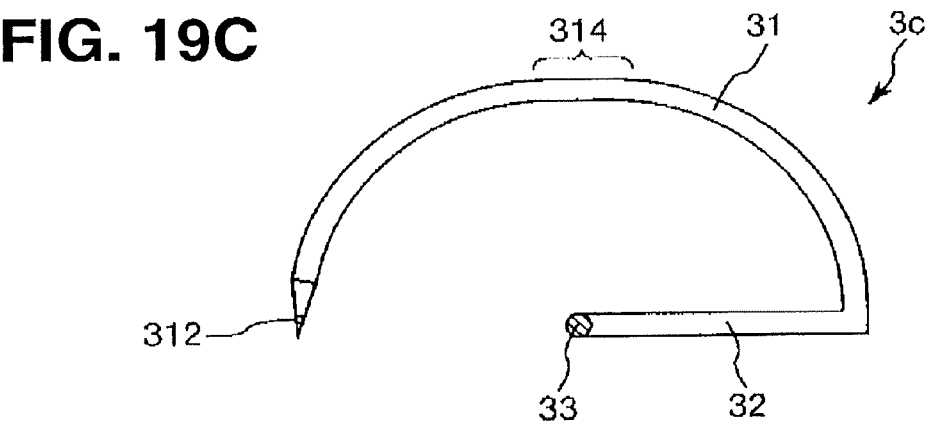

The puncture needle 31 of the puncture member 3*c* shown in FIG. 19C includes a linear shaped portion 314 forming a linear shape on the midway portion of the needle, that is, at the intermediate portion of the puncture needle 31.

It is possible to use this puncture member 3*c* preferably in a case in which the urethra of the patient is positioned at a shallow place from her body surface.

Figure 12:
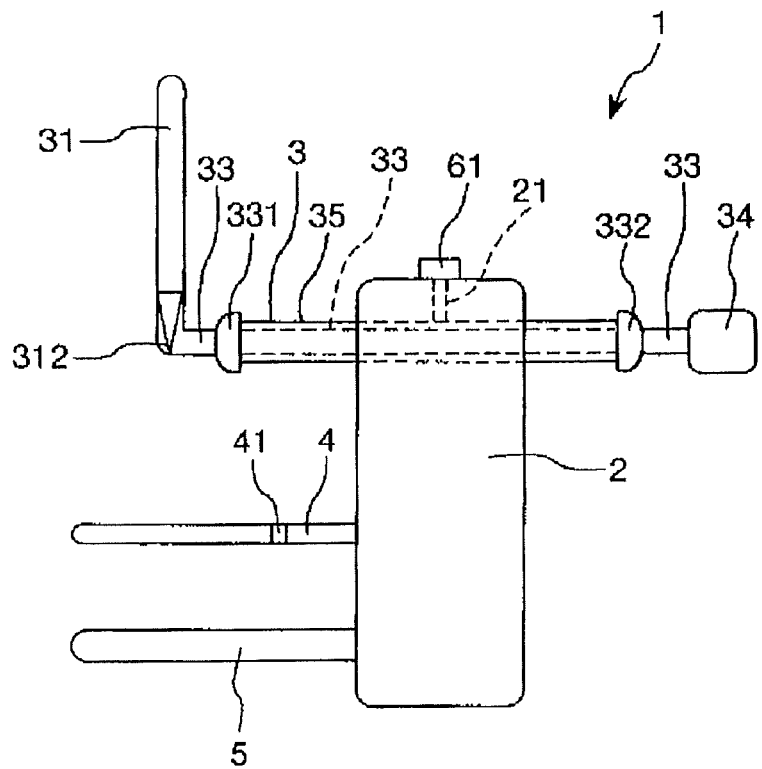
FIG. 12 is a side view of a second embodiment, disclosed by way of example, of a puncture apparatus disclosed here.

FIG. 12 illustrates a second embodiment representing another example of the puncture apparatus disclosed here. The following description of this embodiment will be set forth assuming that the left side in FIG. 12 is the "distal end" and the right side in FIG. 12 is the "proximal end".

The following description of the second embodiment will focus primarily on aspects or features of the puncture apparatus different from those of the first embodiment described above. Features and aspects of this second embodiment of the puncture apparatus that are similar to those described above in the first embodiment are identified by common reference numerals, and a detailed description of such aspects and features is not repeated.

As shown in FIG. 12, in the puncture apparatus 1' of the second embodiment, the axial portion 33 of the puncture member 3 is supported movably by the supporting member 2 in the axial direction of the axial portion 33, that is, in the axial direction of the urethral-insertion member 4.

Specifically, the puncture member 3 includes a tubular body 35 through which an axial portion 33 is inserted and which rotatably supports that axial portion 33. Also, the flanges 331, 332 are arranged on the distal side and on the proximal side of the tubular body 35 respectively, and owing to these flanges 331, 332, the movement in the axial direction of the axial portion 33 with respect to the tubular body 35 is blocked. That is, the flanges 331, 332 permit axial movement of the tubular body 35 relative to the supporting member 2, but limit the amount of such axial movement. The tubular body 35 is placed (mounted) on the supporting member 2 movably in the axial direction of the axial portion 33, that is, in the axial direction of the urethral-insertion member 4.

By moving the puncture member 3 in the axial direction of the urethral-insertion member 4, it is possible for the puncture needle 31 to be disposed in the axial direction of the urethral-insertion member 4 at any position, including on the proximal side of the distal-most tip of the urethral-insertion member 4, at the same position as that of the distal-most tip of the urethral-insertion member 4, and on the distal side of the distal-most end of the urethral-insertion member 4.

Also, the puncture apparatus 1' includes a male screw 61. At the positional region of the supporting member 2 corresponding to that of the tubular body 35, there is formed a female screw portion 21 having a female screw to threadably engage the male screw 61.

When rotating the male screw 61 in a predetermined direction, the distal end of that male screw 61 pressure-contacts the tubular body 35, and the movement of the tubular body 35 with respect to the supporting member 2 is blocked. Also, when rotating the male screw 61 in the reverse direction with respect to the abovementioned direction, the distal end of that male screw 61 is separated from the tubular body 35 and the movement of the tubular body 35 with respect to the supporting member 2 becomes possible.

The male screw 61 and the female screw portion 21 constitute a lock unit for changing-over between a state in which the tubular body 35 is movable with respect to the supporting member 2 and a state in which the movement of the tubular body 35 is blocked.

Also, on the outer circumferential surface of the tubular body 35, there is provided a scale which indicates a distance from a reference position of the center 311 of the puncture needle 31 in the axial direction of the axial portion 33 (regarding the center 311, see FIG. 2).

Also, the urethral-insertion member 4 is a solid bar-shaped member. The distal portion of the urethral-insertion member 4 is rounded. Thus, it is possible to insert the urethral-insertion member 4 smoothly into the inside of the urethra. Needless to say, it is possible for the urethral-insertion member 4 to be formed similarly as that of the first embodiment.

This second embodiment of the puncture apparatus 1' is able to obtain similar effects as those of the aforementioned first embodiment.

Figure 13:
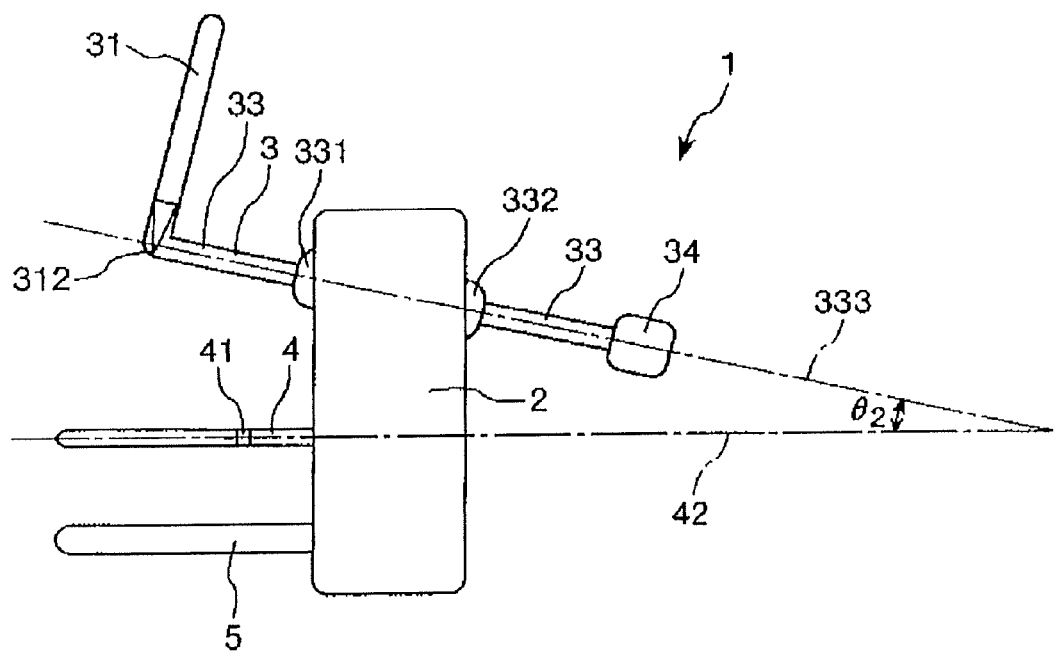
FIG. 13 is a side view of a third embodiment, disclosed by way of example, of a puncture apparatus disclosed here.

FIG. 13 illustrates a third embodiment representing another example of the puncture apparatus disclosed here. The following description of this embodiment will be set forth assuming that the left side in FIG. 13 is the "distal end" and the right side in FIG. 13 is the "proximal end".

The following description of the third embodiment will focus primarily on aspects or features of the puncture apparatus different from those of the first embodiment described above. Features and aspects of this embodiment that are similar to those described above in the first embodiment are identified by common reference numerals, and a detailed description of such aspects and features is not repeated.

As shown in FIG. 13, in the puncture apparatus 1" of the third embodiment, the axis 333 of the axial portion 33 of the puncture member 3 is inclined with respect to the axis 42 such that the distance of separation between the axis 333 and the axis 42 of the urethral-insertion member 4 increases toward the distal side. Thus, it is possible to bury the implant 8 by being inclined.

The axis 42 of the urethral-insertion member 4 and the axis of the vaginal-insertion member 5 are parallel, and the axis 333 of the axial portion 33 of the puncture member 3 is inclined with respect to the axis of the vaginal-insertion member 5 such that the distance of separation between the axis 333 and the axis of the vaginal-insertion member 5 increases toward the distal side.

It is preferable for the inclination-angle θ2 of the axis 333 with respect to the axis 42 to be around 20° to 60°, more preferably around 30° to 45°, and still more preferably around 35° to 40°. Thus, it is possible to carry out the puncture of the puncture needle 31 relatively easily, and concurrently it is possible to realize a shorter puncture-distance.

To explain in more detail, by setting the inclination angle θ2 to be within the aforesaid range, it is possible for the puncture needle 31 to widely capture the right-left obturator foramens 400a, 400b of the pelvis planarly and it is possible to widely secure the puncture space of the puncture needle 31. More specifically, in a state of setting the patient to be at a predetermined body position (dorsosacral position), it is possible to puncture the puncture needle 31 comparatively toward the perpendicular direction with respect to the right-left obturator foramens 400a, 400b of the pelvis. Therefore, it is possible to carry out the puncture of the puncture needle 31 rather easily. In addition, by puncturing the puncture needle 31 comparatively toward perpendicular direction with respect to the obturator foramens 400a, 400b, the puncture needle passes a shallow portion of the tissue, so that it is possible for the needle tip of the puncture needle 31 to pass between the right-left obturator foramens 400a, 400b by a shorter distance. It is possible for the puncture needle 31 to pass comparatively near the pubic-bone connection of the obturator foramens 400a, 400b and preferably through a safety zone, so that it is possible to puncture the region safely in which there are fewer nerves or blood vessels for avoiding injuries. Therefore, there can be obtained a state of lower invasion and it is possible to burden the patient to a lesser degree. In this manner, by setting the inclination angle θ2 in the aforesaid range, it is possible to carry out the puncture of the puncture needle 31 to the patient more properly. On the other hand, in a case in which the inclination angle θ2 is less than the aforesaid lower limit or exceeds the aforesaid upper limit, depending on the individual differences of the patients, the postures during the procedures and the like, there can occur a situation in which it is not possible for the puncture needle 31 to widely capture the obturator foramens 400a, 400b planarly, a situation in which it is not possible to shorten the puncture path adequately and so on. Therefore, it is preferable for the puncture needle 31 to be punctured toward the perpendicular direction with respect to the right-left obturator foramens 400a, 400b of the pelvis.

Also, by carrying out the puncture in the abovementioned angle, it becomes easier to aim the tissue between the mid-urethra indicating the middle positional portion in the length direction of the urethra and the vagina. The position between the mid-urethra and the vagina is a position suitable as the region at which the implant 8 is to be buried and the treatment of the urinary incontinence is to be carried out. More preferably, if the puncture is carried out in a state of manipulating the position so as to arrange a position of the urethra or the vagina, or both, it is rather easy to puncture a position between the mid-urethra and the vagina. It is preferable to move the urethra or the vagina, or both to the predetermined position before passing the puncture member at the position between the mid-urethra and vagina. Moving the urethra or the vagina, or both may be for example pressing/pulling toward the inside/outside of the body. The means for pushing-in either one of the urethra and the vagina toward the inside of the body moves, for example, the urethral-insertion member 4 and/or the vaginal insertion member 5 toward the inside of the body before the puncture as far as a predetermined position along each of the axes after setting a state in which the insertion member is inserted to a proper position. The urethral-insertion member 4 and/or the vaginal insertion member 5 may have a suction mechanism for sucking the inner wall of the urethra or the vagina. The suction mechanism may hold the position of the urethral-insertion member 4 and/or the vaginal insertion member 5. When the urethral-insertion member 4 and/or the vaginal insertion member 5 may be moved toward the inside or the outside of the body, the urethra and/or the vagina may be moved along the member 4 and/or the member 5. At that time, by attaching a visible marker or such a marker which can be imaged under a noninvasive monitoring of the inside of the body depending on such as X-ray, ultrasound or the like onto the urethral-insertion member 4 and/or onto the vaginal insertion member 5, it is possible to recognize the movement distance of the member.

By puncturing the puncture needle 31 perpendicularly with respect to the right-left obturator foramens 400a, 400b of the pelvis in a state in which the position is prolapsed so as to press at least one of the urethra and the vagina toward the inside of the body, it is possible to form the path at a position suitable for the indwelling of the implant 8.

It is preferable that the orbit of the puncture needle 31 is set so as to pass the safety zone of the right-left obturator foramens 400a, 400b of the pelvis, that at least one of the urethra and the vagina is prolapsed toward the inside of the body such that the orbit is positioned between the mid-urethra and the vagina, and that the path will be formed by executing the puncture along the orbit of the puncture needle 31.

The urethral-insertion member 4 is a solid bar-shaped member. Also, the distal portion of the urethral-insertion member 4 is rounded. Thus, it is possible to insert the urethral-insertion member 4 smoothly into the inside of the urethra. It is possible for the urethral-insertion member 4 to be formed similarly as that of the first embodiment.

The puncture apparatus 1" according to this third embodiment is able to obtain similar effects as those of the first embodiment described above.

It is possible for the axis 42 of the urethral-insertion member 4 and the axis of the vaginal-insertion member 5 not to be parallel to each other.

Figure 20:
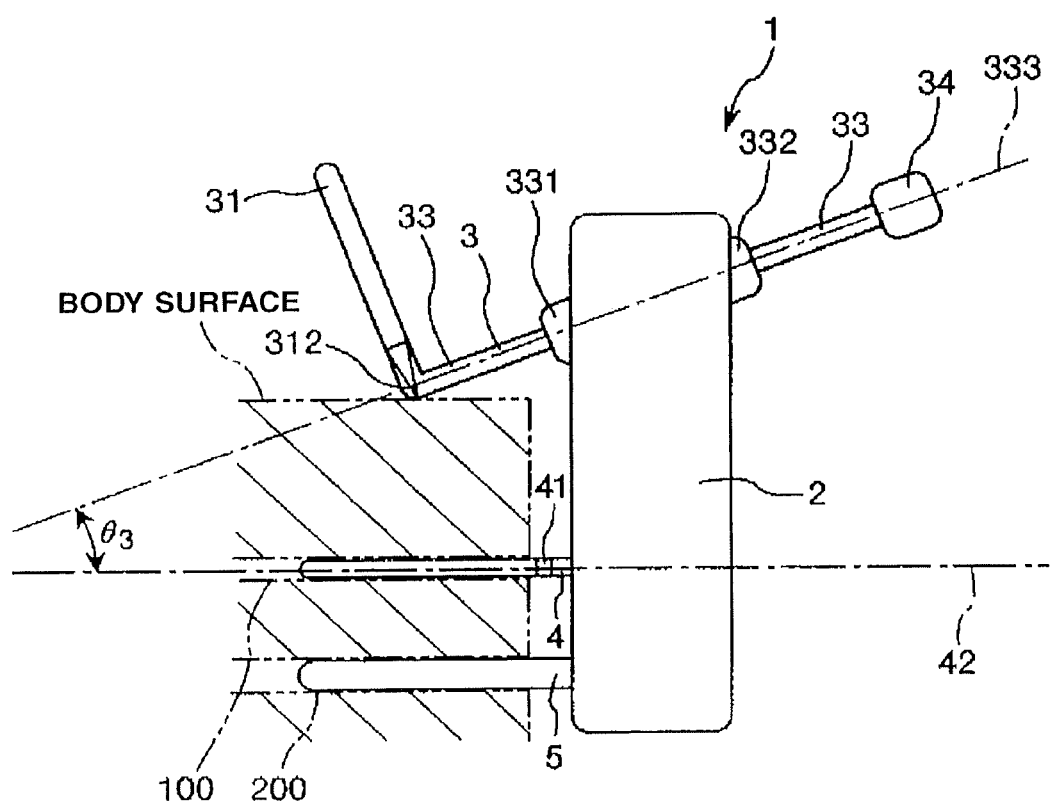
FIG. 20 is a side view of a fourth embodiment, disclosed by way of example, of a puncture apparatus disclosed here.

FIG. 20 illustrates a fourth embodiment representing another example of the puncture apparatus disclosed here. The following description of this embodiment will be set forth assuming that the left side in FIG. 20 is the "distal end" and the right side in FIG. 20 is the "proximal end".

The following description of the fourth embodiment will focus primarily on aspects or features of the puncture apparatus different from those of the third embodiment described above. Features and aspects of this fourth embodiment of the puncture apparatus that are similar to those described above are identified by common reference numerals, and a detailed description of such aspects and features is not repeated.

As shown in FIG. 20, in the puncture apparatus 1' of the fourth embodiment, the axis 333 of the axial portion 33 of the puncture member 3 is inclined with respect to the axis 42 such that the distance of separation between the axis 333 and the axis 42 of the urethral-insertion member 4 decreases toward the distal side. Thus, it is possible to bury the implant 8 by being inclined.

The axis 42 of the urethral-insertion member 4 and the axis of the vaginal-insertion member 5 are in parallel and the axis 333 of the axial portion 33 of the puncture member 3 is inclined with respect to the axis of the vaginal-insertion member 5 such that the separated distance between the axis 333 and the axis of the vaginal-insertion member 5 decreases toward the distal side.

The preferable range of the inclination-angle θ3 of the axis 333 with respect to the axis 42 is similar to the preferable range of the inclination-angle θ2 of the third exemplified embodiment.

This puncture apparatus 1' is able to obtain similar effects as those described above regarding the third embodiment.

Note that the axis 42 of the urethral-insertion member 4 and the axis the vaginal-insertion member 5 are allowed to be not in parallel.

Figure 21:
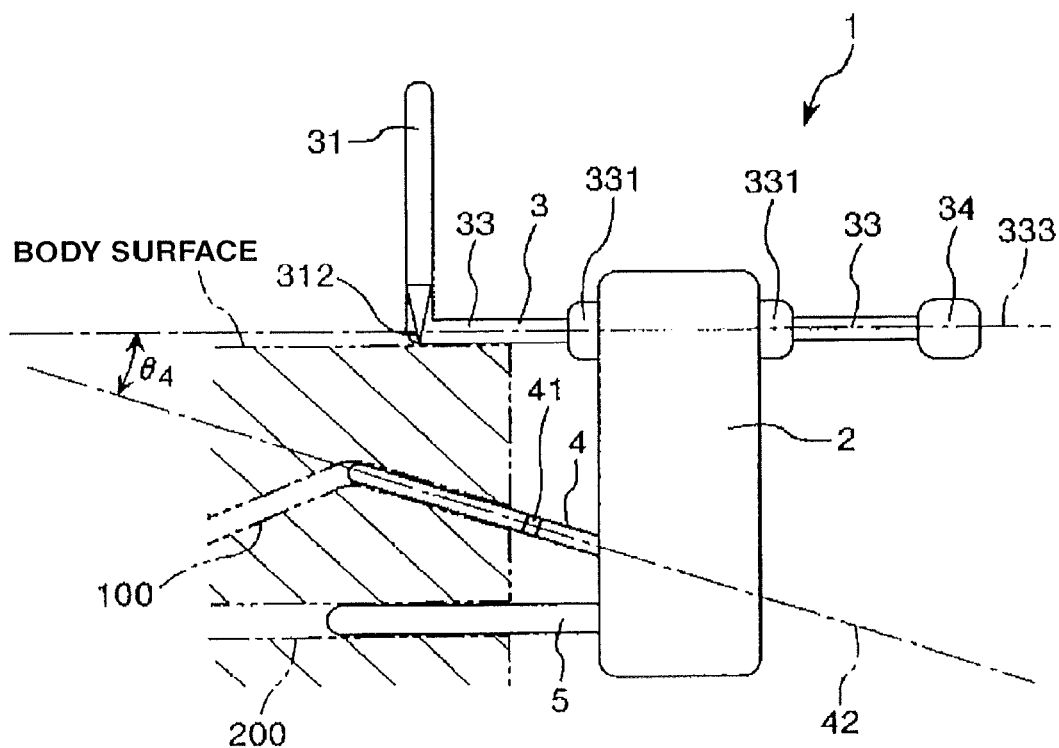
FIG. 21 is a side view of a fifth embodiment, disclosed by way of example, of a puncture apparatus disclosed here

FIG. 21 illustrates a fifth embodiment representing another example of the puncture apparatus disclosed here. The following description of this embodiment will be set forth assuming that the left side in FIG. 21 is the "distal end" and the right side in FIG. 21 is the "proximal end".

The following description of the fifth embodiment will focus primarily on aspects or features of the puncture apparatus different from those of the third embodiment described above. Features and aspects of this embodiment that are similar to those described above in the third embodiment are identified by common reference numerals, and a detailed description of such aspects and features is not repeated.

As shown in FIG. 21, in the puncture apparatus 10 of the fifth embodiment, the axis 42 of the urethral-insertion member 4 is inclined with respect to the axis 333 such that the distance of separation between the axis 42 and the axis 333 of the axial portion 33 of the puncture member 3 decreases toward the distal side. In other words, the axis 333 of the axial portion 33 of the puncture member 3 is inclined with respect to the axis 42 such that the distance of separation between the axis 333 and the axis 42 of the urethral-insertion member 4 decreases toward the distal side. Thus, it is possible to bury the implant 8 by being inclined.

The axis 333 of the axial portion 33 of the puncture member 3 and the axis of the vaginal-insertion member 5 are parallel, and the axis 42 of the urethral-insertion member 4 is inclined with respect to the axis of the vaginal-insertion member 5 such that the distance of separation between the axis line 333 and the axis line of the vaginal-insertion member 5 increases toward the distal side.

The preferable range of the inclination-angle θ4 of the axis line 42 with respect to the axis 333 (inclination-angle of the axis 333 with respect to the axis 42) is similar to the preferable range of the inclination-angle θ2 discussed above regarding the third embodiment.

This puncture apparatus 10 is able to obtain similar effects as those described above regarding the third embodiment.

It is possible for the axis 42 of the urethral-insertion member 4 to be inclined with respect to the axis 333 such that the distance of separation between the axis 42 and the axis 333 of the axial portion 33 of the puncture member 3 increases toward the distal side. In other words, it is possible for the axis 333 of the axial portion 33 of the puncture member 3 to be inclined with respect to the axis 42 such that the distance of separation of the axis 333 and the axis 42 of the urethral-insertion member 4 increases toward the distal side.

Figure 14:
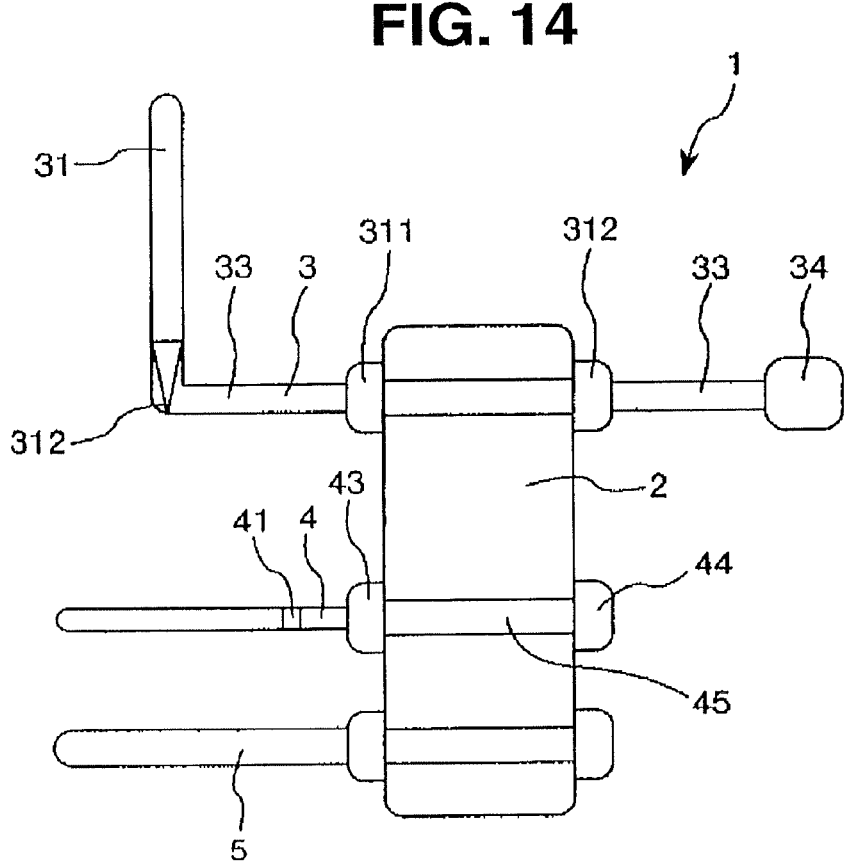
FIG. 14 is a side view of a sixth embodiment, disclosed by way of example, of a puncture apparatus disclosed here.
Figure 15:
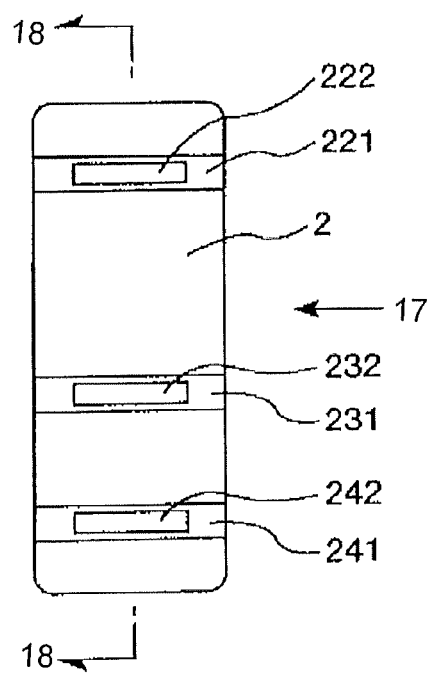
FIG. 15 is a side view showing a supporting member of the puncture apparatus shown in FIG. 14.

FIGS. 14-18 illustrate a sixth embodiment representing another example of the puncture apparatus disclosed here. FIG. 16A is a front elevational view, that is, a view seen from the upside in FIG. 14. Also, either one of FIG. 16B and FIG. 16C is a view seen from a direction of an arrow 16B, 16C in the urethral-insertion member shown in FIG. 16A, in which for the attachment piece of the urethral-insertion member shown in FIG. 16C, there is shown a state thereof in which the attachment piece is rotated by 90° with respect to the attachment piece of the urethral-insertion member shown in FIG. 16B. The following explanation is set forth assuming that the left side in FIG. 14, FIG. 15, FIG. 16A is the "distal end" and the right side is the "proximal end".

The following description of the sixth embodiment will focus primarily on aspects or features of the puncture apparatus different from those of the first embodiment described above. Features and aspects of this embodiment that are similar to those described above in the first embodiment are identified by common reference numerals, and a detailed description of such aspects and features is not repeated.

In the puncture apparatus 10' of the sixth embodiment shown in FIG. 14, the puncture member 3, the urethral-insertion member 4 and the vaginal-insertion member 5 are freely detachable with respect to supporting member 2 respectively. More specifically, the axial portion 33 of the puncture member 3, the urethral-insertion member and the vaginal-insertion member 5 are supported by the supporting member 2 in a freely detachable manner respectively.

Also, the urethral-insertion member 4 is a solid bar-shaped member, and the distal portion of the urethral-insertion member 4 is rounded. Thus, it is possible to insert the urethral-insertion member 4 smoothly into the inside of the urethra. Needless to say, it is possible for the urethral-insertion member 4 to be formed similar to that of the first embodiment described above.

As shown in FIG. 14, FIG. 15, FIG. 17 and FIG. 18, the supporting member 2 includes a groove 221 to which the puncture member 3 is attached or in which the puncture member 3 is positioned; a through-hole 222 provided in the inside of the groove 221; a groove 231 to which the urethral-insertion member 4 is attached or in which the urethral-insertion member 4 is positioned; a through-hole 232 provided in the inside of the groove 231; a groove 241 to which the vaginal-insertion member 5 is attached or in which the vaginal-insertion member 5 is positioned; and a through-hole 242 provided in the inside of the groove 241. The grooves 221, 231, 241 are formed respectively on the front side of the supporting member 2 in the FIG. 15 illustration and extend from the distal end to the proximal end of the supporting member 2.

The construction or configuration of the detachable mechanisms of the puncture member 3, the urethral-insertion member 4 and the vaginal-insertion member 5 with respect to the supporting member 2 is similar to one another, so that hereinafter, with regard to each detachable arrangement, the detachable mechanism of the urethral-insertion member 4 will be explained representatively.

As shown in FIG. 14 and FIG. 16, in a state of being attached to the supporting member 2 (hereinafter, also referred to as "attachment state"), the urethral-insertion member 4 is formed with a flange 43 and a flange 44 on the distal side and on the proximal side respectively through that supporting member 2, and the axial movement of the urethral-insertion member 4 with respect to the supporting member 2 is blocked by these flanges 43, 44. The flange 44 is arranged at the proximal portion of the urethral-insertion member 4.

Also, a region 45 between the flange 43 and the flange 44 of the urethral-insertion member 4 is thicker than the region on the distal side from the flange 43 of the urethral-insertion member 4. Also, the cross-sectional shape of the region 45 between the flange 43 and the flange 44 of the urethral-insertion member 4 is square shape according to the constitution shown in the drawing.

Figure 16A:
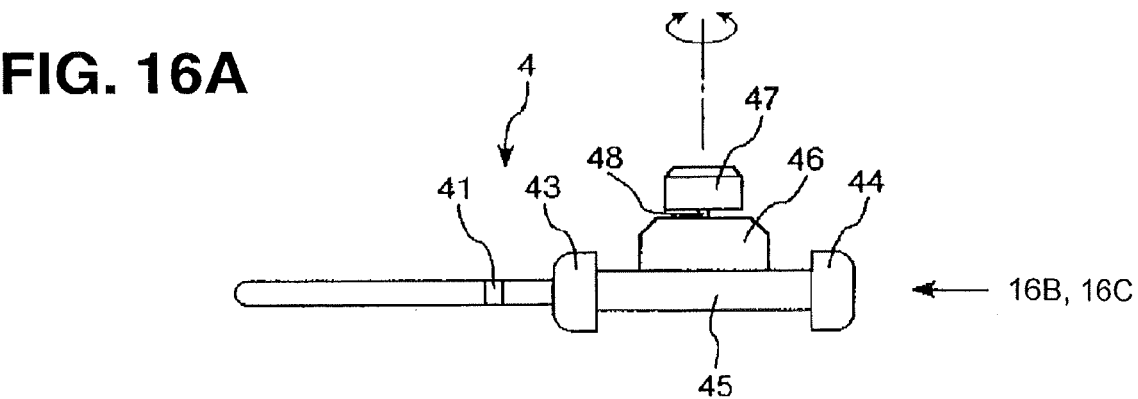
FIGS. 16A to 16C are views showing a urethral-insertion member of the puncture apparatus shown in FIG. 14.

At the region 45 between the flange 43 and the flange 44 of the urethral-insertion member 4, there is formed a protruding portion 46, in the attachment state, which protrudes toward the rear side from the front side of the drawing of FIG. 14, that is, which protrudes toward the upper side in FIG. 16A. At the protruding portion 46, there is located an attachment piece 48 through a freely rotatable axis member 47. This attachment piece 48 has a flattened shape. The attachment piece 48 protrudes toward the upper side in FIG. 16A.

Figure 16B:
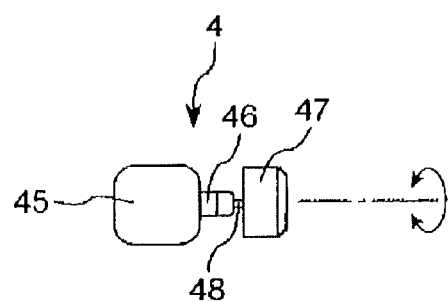
Figure 16C:
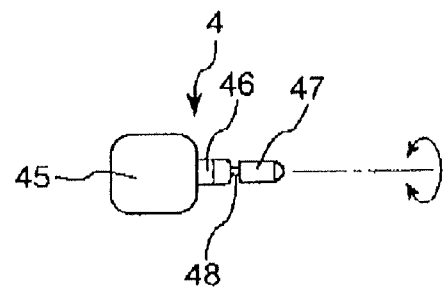
Figure 17:
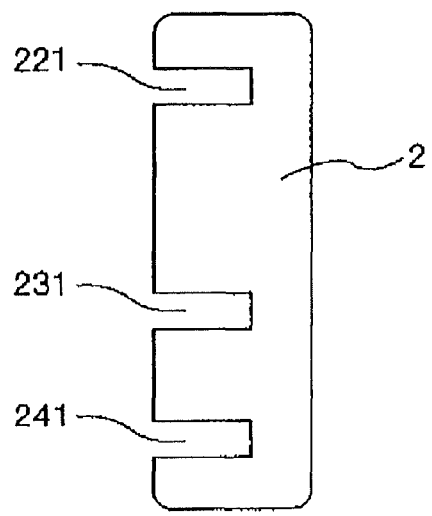
FIG. 17 is a view seeing the puncture apparatus from a direction of an arrow 17 shown in FIG. 15.

When attaching the urethral-insertion member 4 to the supporting member 2, the attachment piece 48 of the urethral-insertion member 4 is set in a state shown in FIG. 16C and the attachment piece 48 is inserted from the groove 231 of the supporting member 2 and is passed through the through-hole 232. Then, at that time, the region 45 between the flange 43 and the flange 44 of the urethral-insertion member 4 is inserted into the groove 231 of the supporting member 2 and concurrently, the protruding portion 46 is inserted into the through-hole 232.

Figure 18:
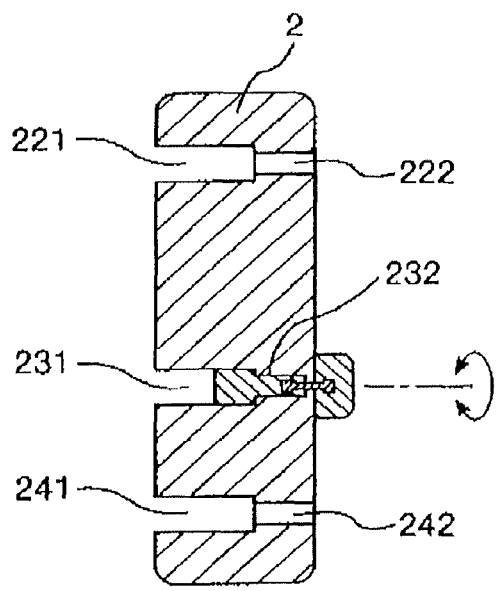
FIG. 18 is a cross-sectional view along the section line 18-18 in FIG. 15.

Next, as shown in FIG. 18, the attachment piece 48 of the urethral-insertion member 4 is set in a state shown in FIG. 16B by being rotated by 90°. Thus, while the region 45 between the flange 43 and the flange 44 of the urethral-insertion member 4 is attached onto or set into the bottom surface of the groove 231, the attachment piece 48 is attached or set onto the surface on the right side of the urethral-insertion member 4 in FIG. 18 and so the attachment and detachment of the urethral-insertion member 4 with respect to the supporting member 2 is blocked.

Also, when removing the urethral-insertion member 4 from the supporting member, the attachment piece 48 of the urethral-insertion member 4 is set in a state shown in FIG. 16C and the urethral-insertion member 4 is made to move toward the left side in FIG. 18. Thus, it is possible to remove the urethral-insertion member 4 from the supporting member 2.

This puncture apparatus 10' is able to obtain similar effects as those of the first embodiment described above. It is possible to apply this sixth embodiment to the second to fifth embodiments described above to provide the freely detachable arrangement of the puncture member 3, the urethral-insertion member 4 and/or the vaginal-insertion member 5 with respect to the supporting member 2.

In this embodiment, the puncture member 3, the urethral-insertion member 4 and the vaginal-insertion member 5 are freely detachable with respect to the supporting member 2. But the apparatus is not limited to this configuration and it is possible, for example, for only one or only two of the puncture member 3, urethral-insertion member 4 and the vaginal-insertion member 5 to be freely detachable with respect to the supporting member 2. In this case, it is preferable for at least the puncture member 3 to be freely detachable with respect to the supporting member 2.

Figure 22A:
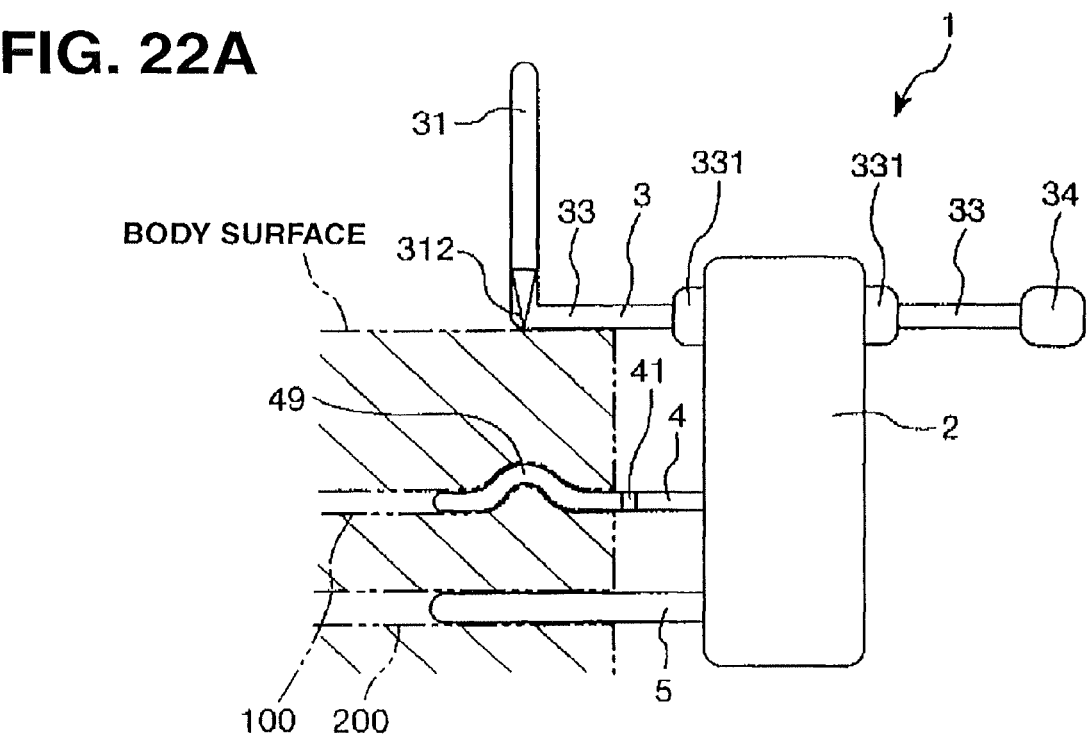
FIGS. 22A to 22C are side views of a seventh embodiment, disclosed by way of example, of a puncture apparatus disclosed here
Figure 22B:
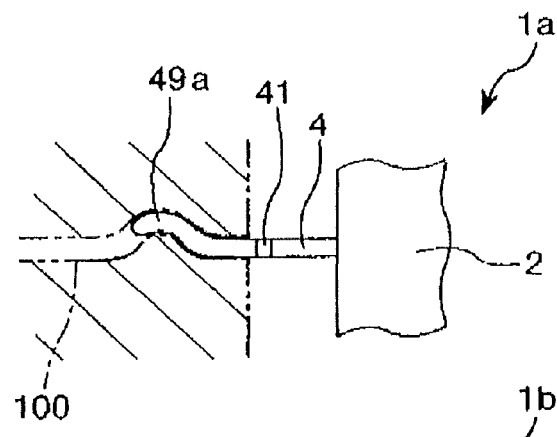
Figure 22C:
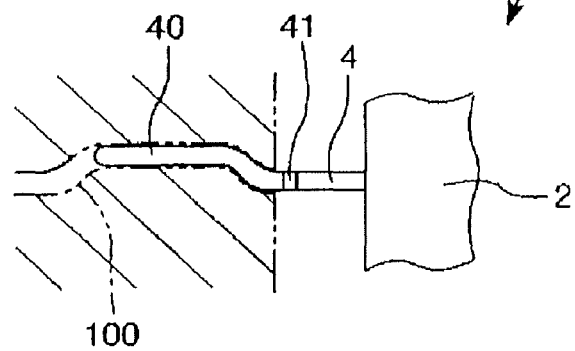

FIGS. 22A-22C illustrates a seventh embodiment representing another example of the puncture apparatus disclosed here. The following description of this embodiment will be set forth assuming that the left side in FIGS. 22A-22C is the "distal end" and the right side in FIGS. 22A-22C is the "proximal end".

The following description of the seventh embodiment will focus primarily on aspects or features of the puncture apparatus different from those of the first embodiment described above. Features and aspects of this embodiment that are similar to those described above in the first embodiment are identified by common reference numerals, and a detailed description of such aspects and features is not repeated.

As shown in FIG. 22A, in the puncture apparatus 10' of the seventh embodiment, the urethral-insertion member 4 is configured so that a midway portion of the urethral-insertion member 4 is bent and includes a protruding portion 49 which protrudes toward the direction away from the vaginal-insertion member 5.

It is possible by this protruding portion 49 to widen the distance between the urethra 100 and the vagina 200 and thus, it is possible to reliably prevent a phenomenon in which the puncture needle 31 will puncture the urethra 100 or the vaginal wall of the vagina 200. Similar effects are obtained by the puncture apparatuses 10'a, 10'b described below.

In the puncture apparatus 10'a shown in FIG. 22B, the length of the urethral-insertion member 4 becomes short with respect to that of the puncture apparatus 10' shown in FIG. 22A and there is included a protruding portion 49a at the distal portion of the urethral-insertion member 4. The protruding portion 49a is a portion which is formed by bending the urethral-insertion member 4 and which protrudes toward the direction apart from the vaginal-insertion member 5, in which it is constituted to be shorter than the protruding portion 49 of the puncture apparatus 1.

In this puncture apparatus 10'a, it is possible to prevent an excessive insertion of the urethral-insertion member 4 into the urethra 100.

In the puncture apparatus 10'b shown in FIG. 22C, the urethral-insertion member 4 includes a linear shaped portion 40 forming a linear shape which is positioned at the regional portion from the midway to the distal end thereof and which is on the side apart from the vaginal-insertion member 5 compared with the proximal portion. Note that there is no limitation in particular for the length of the linear shaped portion 40 and the length is set arbitrarily in response to various conditions.

These puncture apparatuses 10', 10'a, 10'b are able to obtain similar effects as those described above regarding the first embodiment. And it is possible to apply this seventh embodiment to the other respective embodiments described above.

Figure 23:
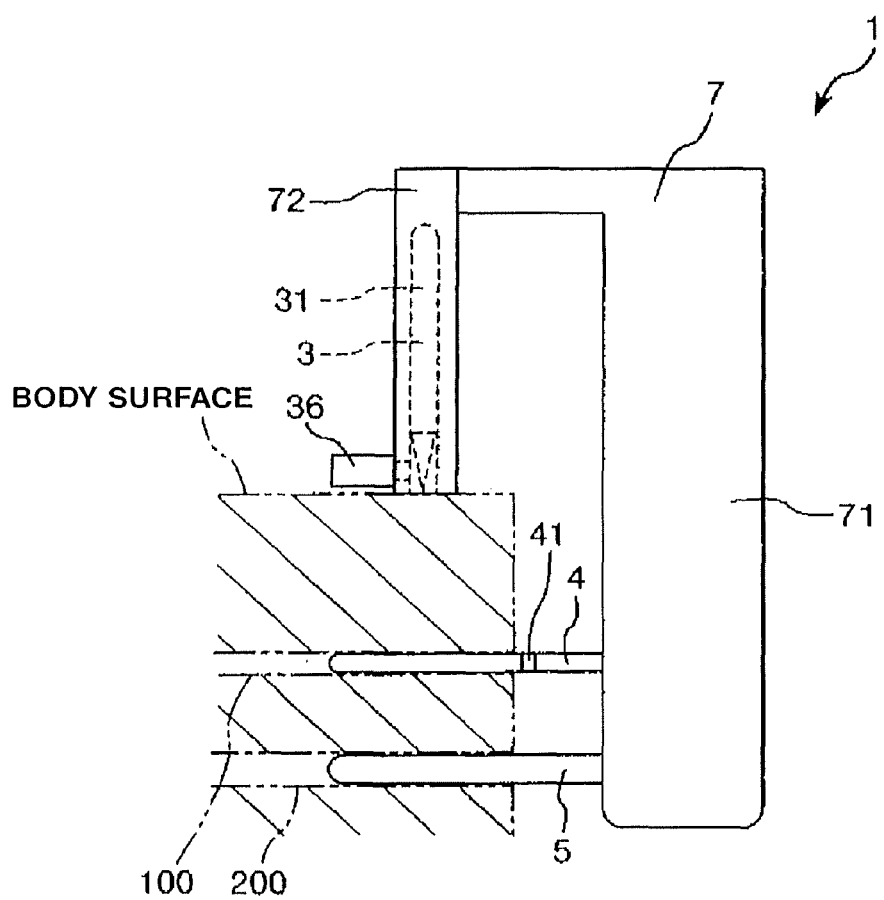
FIG. 23 is a side view of an eighth embodiment, disclosed by way of example, of a puncture apparatus disclosed here
Figure 24:
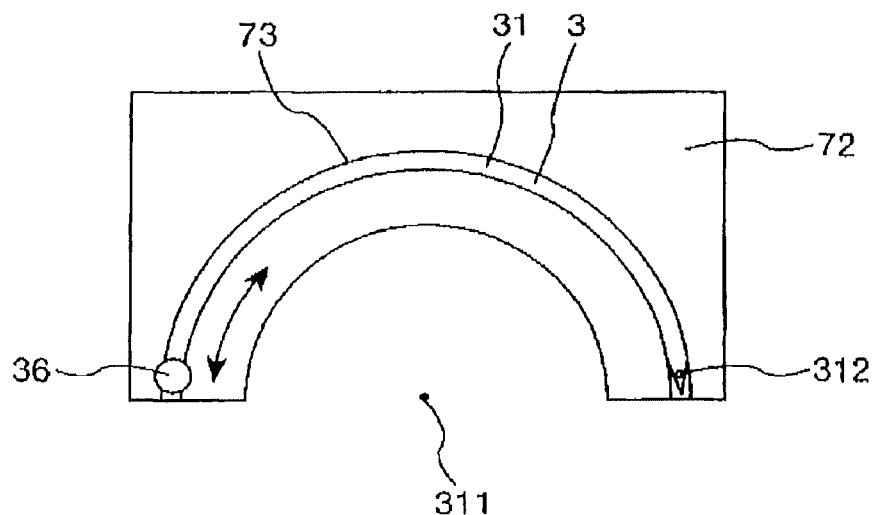
FIG. 24 is a front elevational view showing a puncture member and a second supporting portion of the puncture apparatus shown in FIG. 23.

FIGS. 23 and 24 illustrate an eighth embodiment representing another example of the puncture apparatus disclosed here, with FIG. representing a side view of the apparatus and FIG. 24 showing a puncture member and a second supporting portion of the puncture apparatus shown in FIG. 23 as seen from the front. The following description of this embodiment will be set forth assuming that the left side in FIG. 23 is the "distal end" and the right side in FIG. 23 is the "proximal end".

The following description of the eighth embodiment will focus primarily on aspects or features of the puncture apparatus different from those of the first embodiment described above. Features and aspects of this embodiment that are similar to those described above in the first embodiment are identified by common reference numerals, and a detailed description of such aspects and features is not repeated.

As shown in FIG. 23 and FIG. 24, in the puncture apparatus 10" of the eighth embodiment, a supporting member (restriction means) 7 includes a first supporting portion 71 for supporting the urethral-insertion member 4 and the vaginal-insertion member 5; and a second supporting portion 72 on the distal side of the first supporting portion 71 and which freely rotatably supports the puncture member 3.

The puncture member 3 includes a puncture needle 31 and a grasping unit 36 provided at the proximal portion of the puncture needle 31. The grasping unit 36 protrudes toward the distal side from the proximal portion of the puncture needle 31, that is, toward the left side in FIG. 23.

In the second supporting portion 72, there is formed a groove (arc-shaped groove) 73 having a shape corresponding to the puncture needle 31, and the puncture needle 31 is inserted (housed) inside the groove 73 in a freely rotatable or freely movable manner. More specifically, the puncture needle 31 is configured and housed to slide along the inner surface of the groove 73, and the puncture needle 31 moves rotationally (along an arc), with the center 311 serving as the rotary center by sliding along the inner surface of the groove 73. The second supporting portion 72 thus serves as a guide member for guiding the puncture needle 31 along the groove 73. When moving the puncture needle 31, that is, the puncture member 3 rotationally, the grasping unit 36 is grasped and the rotational operation of the puncture member is carried out. Regarding the center 311, it is possible to apply the features of axial portion 33 in the other embodiments.

The inside of the groove 73 is larger than the opening of the entrance to the groove. It is thus possible to prevent the puncture needle 31 from dropping-out from the inside of the groove 73 (e.g., by configuring the portion of the needle positioned in the groove to be slightly larger than the size of the opening of the entrance of the groove).

This puncture apparatus 10" obtains similar effects as those described above regarding the first embodiment. It is possible to apply this eighth embodiment to the respective other embodiments described above.

The guide member is not limited to the specific member used in this embodiment. It is possible, for example, to employ members described below and referred to as constitution 1, constitution 2 and constitution 3.

In constitution 1, a convex portion (guide portion) is provided on the puncture needle, the puncture needle is not housed in the groove of a guide member, the convex portion is housed in the guide member, and this convex portion is guided along the groove.

In constitution 2, the guide member includes, for example, a rail (rib) forming an arc shape, and there is provided, on the puncture needle, a guide portion which is engaged with the rail and which is movable along this rail. The guide portion is guided along the rail.

In constitution 1, the guide member includes a plurality of pin-pairs constituted by pin-pairs each of which is arranged by being separated as much as a predetermined distance, for example, a distance which is a little bit longer than the outer diameter of the puncture needle and the puncture needle is configured to move between each of the pin-pairs. The respective pin pairs are arranged, for example, in an arc shape and the puncture needle is guided by these respective pin-pairs.

Figure 25:
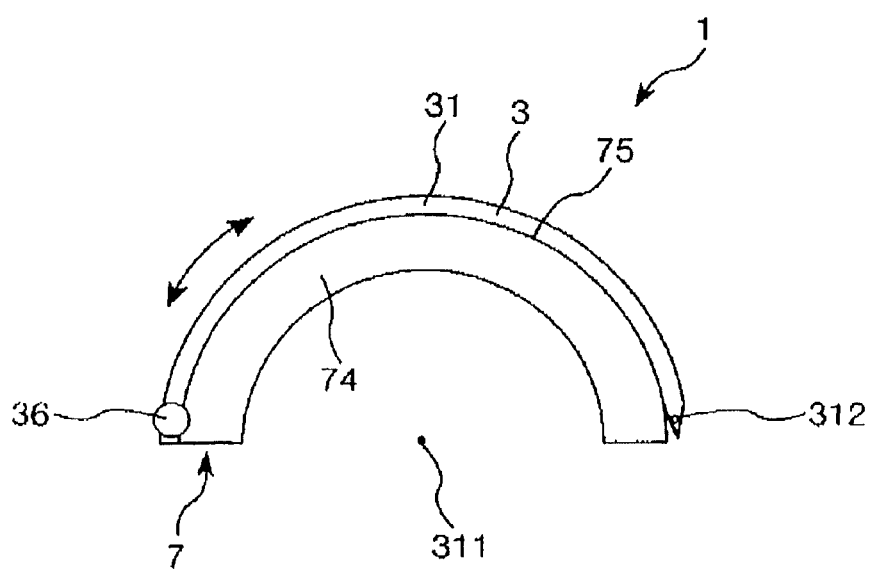
FIG. 25 is a front elevational view showing a puncture member and a second supporting portion of a supporting member in a ninth embodiment of the puncture apparatus disclosed here.

FIG. 25 illustrates a puncture member and a second supporting portion of a supporting member in a ninth embodiment of the puncture apparatus disclosed here. In the description below, the upper side in FIG. 25 is "up" and the lower side is "down".

The following description of the ninth embodiment will focus primarily on aspects or features of the puncture apparatus different from those of the eighth embodiment described above. Features and aspects of this embodiment that are similar to those described above in the eighth embodiment are identified by common reference numerals, and a detailed description of such aspects and features is not repeated.

As shown in FIG. 25, in the puncture apparatus 10''' in the ninth embodiment, a second supporting portion 74 of the supporting member 7 forms an arc shape. More specifically, an upper surface 75 of the second supporting portion 74 forms a shape corresponding to the puncture needle 31.

Also, the puncture needle 31 is placed or positioned on the upper surface 75 of the second supporting portion 74. The puncture needle 31 is slidable along the upper surface 75 of the second supporting portion 74, and the puncture needle 31 moves rotationally (along an arc) by making the center 311 thereof as the rotary center by sliding along the upper surface 75. The second supporting portion 72 thus constitutes the guide member.

This puncture apparatus 10''' is able to obtain similar effects as those described above regarding the eighth embodiment. And it is possible to apply this ninth embodiment to the respective other embodiments described above.

As described above, the puncture apparatus disclosed here is explained based on the embodiments shown in the drawings, but the present invention is not limited by these embodiments, and it is possible to replace the constitution of each portion by a different or arbitrary constitution having a similar function. It is also possible to add other arbitrary constituent elements.

Figure 26:
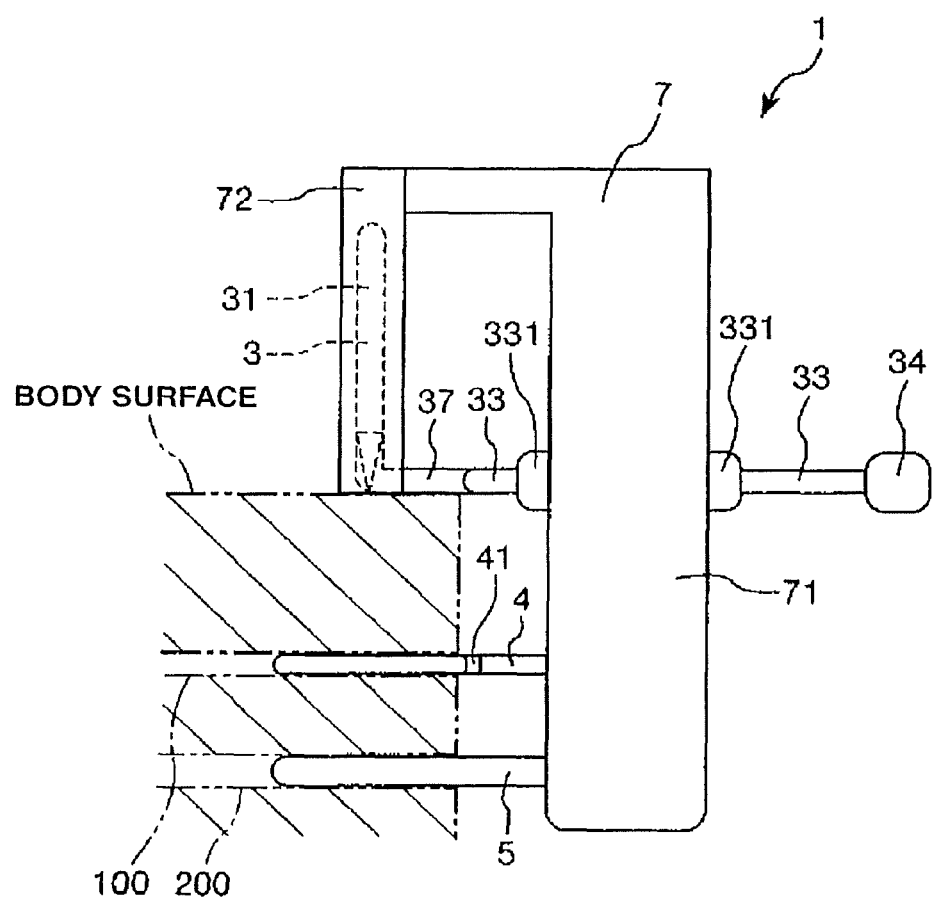
FIG. 26 is a side view showing another example of the puncture apparatus of the present invention.
Figure 27:
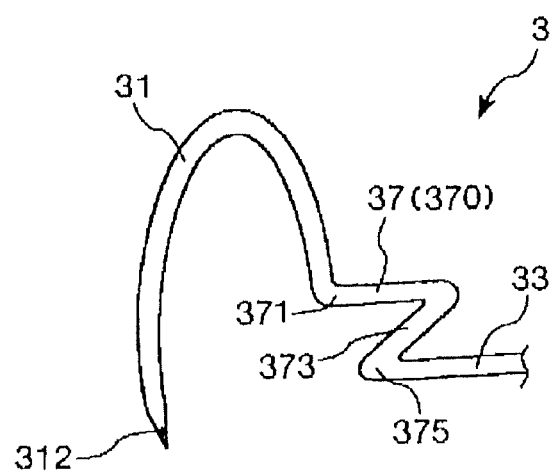
FIG. 27 is a perspective view showing a puncture member of the puncture apparatus shown in FIG. 26.

Also, it is possible to employ an arrangement in which two or more constructions or constitutions within the respective embodiments are combined. In particular, as shown in FIG. 26, by combining the first embodiment (see FIG. 1 and FIG. 2) and the eighth embodiment (see FIG. 23 and FIG. 24) and by providing the second supporting portion 72 of the eighth embodiment, which supports the puncture member 3 in a freely rotatable manner, in the puncture apparatus 1 of the first embodiment, it is possible to restrict the orbit exactly when puncturing the living body tissue by the puncture member 3 and thus, a more accurate puncture becomes possible. The interlock portion 37 of the puncture member 3 of the puncture apparatus 1, which is shown in this FIG. 26, forms an L-shape as shown in FIG. 27. The axial portion 33 of the puncture member 3 is located or mounted on the first supporting portion 71 in a freely rotatable manner.

Here, depending on the patient, the region, between the position at which the puncture needle 31 is inserted into (enters) the body from the body surface and the position at which the needle protrudes back outside the body from the body surface, rises and the center of the arc of the puncture needle 31 is positioned at the patient side compared with the body surface of the patient, so that there may be a situation in which the puncture apparatus 1 cannot be correctly placed at a predetermined position. Such a rising can be seen many times for heavy patients. On the other hand, for a skinny patient or the like, caused by the fact that the interlocking region or the vicinity of such region is depressed, it becomes a state in which there occurs a phenomenon of rising relatively and there occurs a situation in which the center portion of the patient interferes with the puncture needle 31, so that a situation arises in which that state prevents the puncture operation. Even in such a case, by setting the interlock portion 37 to be in an L-shape, it is possible to help prevent the interlock portion 37 and the axis portion 33 from interfering with the rising region of the patient and it is possible to carry out the puncture operation by the puncture needle 31 rather easily and also reliably. The interlock portion 37 is composed of a distal portion 371 and a proximal portion 373.

The distal portion 371 extends from the end portion at the opposite side of the needle tip of the puncture needle 31 toward the perpendicular direction with respect to the plane including the arc of the puncture member 3 (with respect to the plane on which the puncture member 3 moves rotationally) (with respect to the orbital plane of the arc). The proximal portion 373 extends from the proximal portion of the distal portion 371 in the perpendicular direction toward the axial portion 33. More specifically, the proximal portion 373 extends from the proximal portion of the distal portion 371 in a direction perpendicular to the axial portion 33. The axial portion 33 extends perpendicularly from the center of the arc of the puncture needle 31 with respect to the plane including the arc of the puncture member 3.

It is also possible for the puncture apparatus 10''' shown in FIG. 26 to use one of the urethral-insertion member and the vaginal insertion member if it is possible to carry out the puncture by avoiding the urethra 100 and the vagina 200 carefully by specifying the positions of the urethra 100 and the vagina 200, for example, by monitoring with X-ray, ultrasound or the like. In this case, it is possible for the puncture apparatus 10''' shown in FIG. 26 to be formed to have constituent elements of a puncture needle 31 which is placed freely rotatably, which includes a bent region and which punctures living body tissue; an axial portion 33 which extends from the end portion at the opposite side of the needle tip of the puncture needle 31 through the L-shaped interlock portion 37; and a supporting portion 71 by which the axial portion 33 is placed freely rotatably.

In the configuration shown in FIG. 27, the interlock portion 37 forms an L-shape, but the shape of the interlock portion 37 is not so limited, and it is possible to employ a configuration which is formed, for example, by a linear shape, a curved shape, a shape made by combining a linear shape and a curved shape, or the like in which the portion is connected to the axial portion 33 so as not to interfere with the region of the rising portion of the aforesaid patient.

Also, in the present invention, it is possible, for example, to employ a configuration in which the vaginal-insertion member is omitted and the restriction means is provided so as to restrict only the positional relation between the puncture needle (puncture member) and the urethral-insertion member.

In the embodiments of the puncture apparatus described above, the orbit or path of movement of the puncture member is specified according to the positional relation with respect to the urethral-insertion member. But it is also possible to specify the orbit or path of movement according to the positional relation with respect to the vaginal insertion member. For example, it is possible to employ a configuration in which the orbit or path of movement of the puncture member passes a position which is on the position side near from the center point of the orbit and which is spaced from the vaginal insertion member by a predetermined distance. Thus, for example, with respect to a patient whose distance between the mid-urethra and the vagina was measured beforehand, it is possible for the orbit or movement path of the puncture member to pass a position which is on the position side near from the center point of the orbit and which is spaced from the vaginal insertion member by a distance shorter than the distance between the mid-urethra and the vagina.

The description above describes various embodiments in which the puncture apparatus is used in an apparatus that buries or positions a buriable implant for treatment of the woman's urinary incontinence into the inside of the living body. But the use of the puncture apparatus is not limited in this regard.

For example, the target to be applied with the puncture apparatus discloses here includes an excretory disorder along with the weakening of the pelvic floor muscle group (urinary urgency, frequent urination, urinary incontinence, fecal incontinence, urinary retention, dysuria or the like), and a pelvic floor disorder including pelvic organ prolapse, vesicovaginal fistula, urethrovaginal fistula, pelvic pain or the like. In the pelvic organ prolapse, there are include disorders of cystocele, enterocele, rectocele, hysterocele and the like. Alternatively, there are included disorders of anterior vaginal prolapse, posterior vaginal prolapse, vaginal vault prolapse, vaginal apical prolapse and the like in which the naming method thereof is based on the manipulating vaginal-wall regions.

Also, in the overactive tissues, there are included bladder, vagina, uterus, bowel and the like. In the lessactive tissues, there are included bones, muscles, fascias, ligaments and the like. In particularly, in the pelvic floor disorders, there are included an obturator fascia, a coccygeus fascia, a cardinal ligament, a uterosacral ligament, a sacrotuberous ligament and the like.

For the procedure for interlocking an overactive tissue in the pelvic floor disorder with the lessactive tissue, there are included a retropubic sling surgery, a transobturator sling surgery (Transobturator Sling surgery, Transobturator Tape: TOT), a tension-free vaginal mesh (Tension-free Vaginal Mesh: TVM) surgery, a uterosacral ligament suspension (Uterosacral Ligament Suspension: USLS) surgery, a sacrospinous ligament fixation (Sacrospinous Ligament Fixation: SSLF) surgery, an iliococcygeus fascia fixation surgery, a coccygeus fascia fixation surgery, and the like.

It is possible for the puncture apparatus disclosed here to be applied to the pelvic floor disorder as follows. It is possible for the puncture apparatus used for the pelvic floor disorder to be applied with the respective constructions of the puncture apparatuses of the above-described embodiments for treating urinary incontinence. As one embodiment, there are provided with a puncture member which is freely rotatably mounted, which includes a bent region and which includes a puncture needle for puncturing living body tissue; an insertion member having a longitudinal shape, which is to be inserted into the inside of the body; and a restriction structure for restricting the positional relation between the puncture member and the insertion member such that the needle tip of the puncture needle will pass at a far-position side from the rotation center of the puncture needle compared with the insertion member when the puncture member rotates and punctures the living body tissue.

For example, in the case of a rectocele, within the pelvic organ prolapses included in the pelvic floor disorders, in which the deviation occurs by the fact that the rectum pushes the vaginal wall, the overactive tissues are the rectum and the vagina and the lessactive tissue becomes the interlock region, or a muscle, a tendon or a ligament in the vicinity thereof.

As an example, one embodiment of a procedure for forming a path for burying an implant for treating the rectocele is as follows. First, a puncture apparatus is prepared and provided with a puncture member which is freely rotatably positioned, and which includes a bent region and which includes a puncture needle for puncturing living body tissue; an insertion member having a longitudinal (elongated) shape, which is to be inserted into the inside of the living body; and a restriction structure for restricting the positional relation between the puncture member and the insertion member such that the needle tip of the puncture needle will pass a far-position side (be spaced from) from the rotation center of the puncture needle compared with the insertion member when the puncture member rotates and punctures the living body tissue. Next, the insertion member is inserted into a rectum of a patient. Further, the puncture needle of the puncture member is operated to puncture a body surface at one buttock region of the patient or at the region in the vicinity thereof, made to enter into the body, made to pass a far-position side of the rectum, made to protrude to the outside of the body from the body surface of another buttock region or from the region in the vicinity of such region, whereby there is formed a through-hole reaching the far-position side of the rectum and the another buttock region or the region in the vicinity of such region from the other buttock region or the region in the vicinity of such region. After forming the through-hole, a mesh-shaped implant is indwelled by an identical or similar method as that of the urinary incontinence described above.

For another embodiment of the procedure disclosed by way of example, there is a method in which there is prepared a puncture member which is freely rotatable, which includes a bent region and which includes a puncture needle for puncturing living body tissue; and when the puncture member is moved rotationally and the puncture needle of the puncture member punctures the living body tissue, the puncture needle is made to puncture a body surface at a buttock region of the patient or at the region in the vicinity thereof and is made to enter into the body; and the puncture member is made to pass a far-position side from the rotation center of the puncture needle compared with a rectum which is the target region, whereby the path is formed.

An another embodiment of the procedure, there is prepared a puncture tool provided with an insertion member having a longitudinal (elongated) shape, which is to be inserted into the inside of a rectum, and a puncture member which can puncture the living body tissue and which has such an orbit or movement path passing a far-position side compared with the insertion member; the insertion member is inserted into the rectum of a patient; the puncture member is made to puncture into the body surface at a buttock region of the patient or at the region in the vicinity of such region; and the puncture member is made to pass a far-position side compared with the insertion member, whereby the path is formed. The insertion member is not limited to a member which is inserted into a tubular lumen having an opening on the surface of the living body, such as a vagina, a urethra, a rectum and the like, and there can be included also a configuration in which the insertion member punctures the tissue from the surface of the living body. In case of puncturing the tissue from the surface of the living body, it is preferable for a tissue insertion member to be provided with a marker by which the position of the tissue insertion member can be confirmed or identified. By providing a marker, there can be confirmed the position at which the insertion member punctures the tissue. For the marker, it is possible to attach a visually-recognizable marker by which the insertion depth is visually recognizable. Also, for the marker, it is preferable to use a marker which is visually recognizable under a noninvasive monitoring inside the body.

The target to be applied is not limited by the pelvic floor disorder. For example, the apparatus and method are also applicable to a disorder in which position deviation of an organ occurs in the inside of the living body such as a case of an interlock hernia, an abdominal wall hernia or the like.

A puncture apparatus disclosed here generally includes a freely rotatable puncture member which includes a bent region and which includes a puncture needle for puncturing living body tissue, a urethral-insertion member having an elongated shape which is to insertable into the inside of a urethra, and restriction means for restricting the positional relation between the puncture member and the urethral-insertion member such that the needle tip of the puncture needle will pass a far-position side from the rotation center of the puncture needle compared with the urethral-insertion member when the puncture member rotates and punctures the living body tissue.

When burying an implant for example, burden onto a patient is relatively small, safety of the patient is quite good and also the safety of the operator is rather high.

When using the puncture apparatus for treating a woman's urinary incontinence, for example, the urethral-insertion member of aforesaid puncture apparatus is inserted into her urethra, the puncture needle is moved rotationally, and her living body is punctured by the puncture needle. At that time, the needle tip of the puncture needle passes a far-position side from the center of the puncture needle compared with the urethral-insertion member, so that it is possible to puncture the living body by avoiding the urethra and it is possible to prevent a phenomenon that the puncture needle is to puncture the urethra. Also, it is possible to prevent a phenomenon that the finger tip of the operator is punctured by the puncture needle.

Also, when burying an implant for treatment of the urinary incontinence, incision of a vagina wall is not necessary and it is possible to bury that implant by a relatively low invasive procedure. Also, it is possible to prevent a phenomenon in which, such as in a case of incising a vagina, the implant will be exposed to the inside of the vagina from a wound caused by the incision and in which there occur complications which are to be caused by an infection from the wound or the like, and it is very safe and it is possible to bury the implant reliably.

Also, similar benefits can be realized for disorders in which a position deviation of an organ occurs in the inside of the living body such as a case of a pelvic floor disorder or the like.

The puncture apparatus and method here thus exhibit industrial usability.

Figure 28:
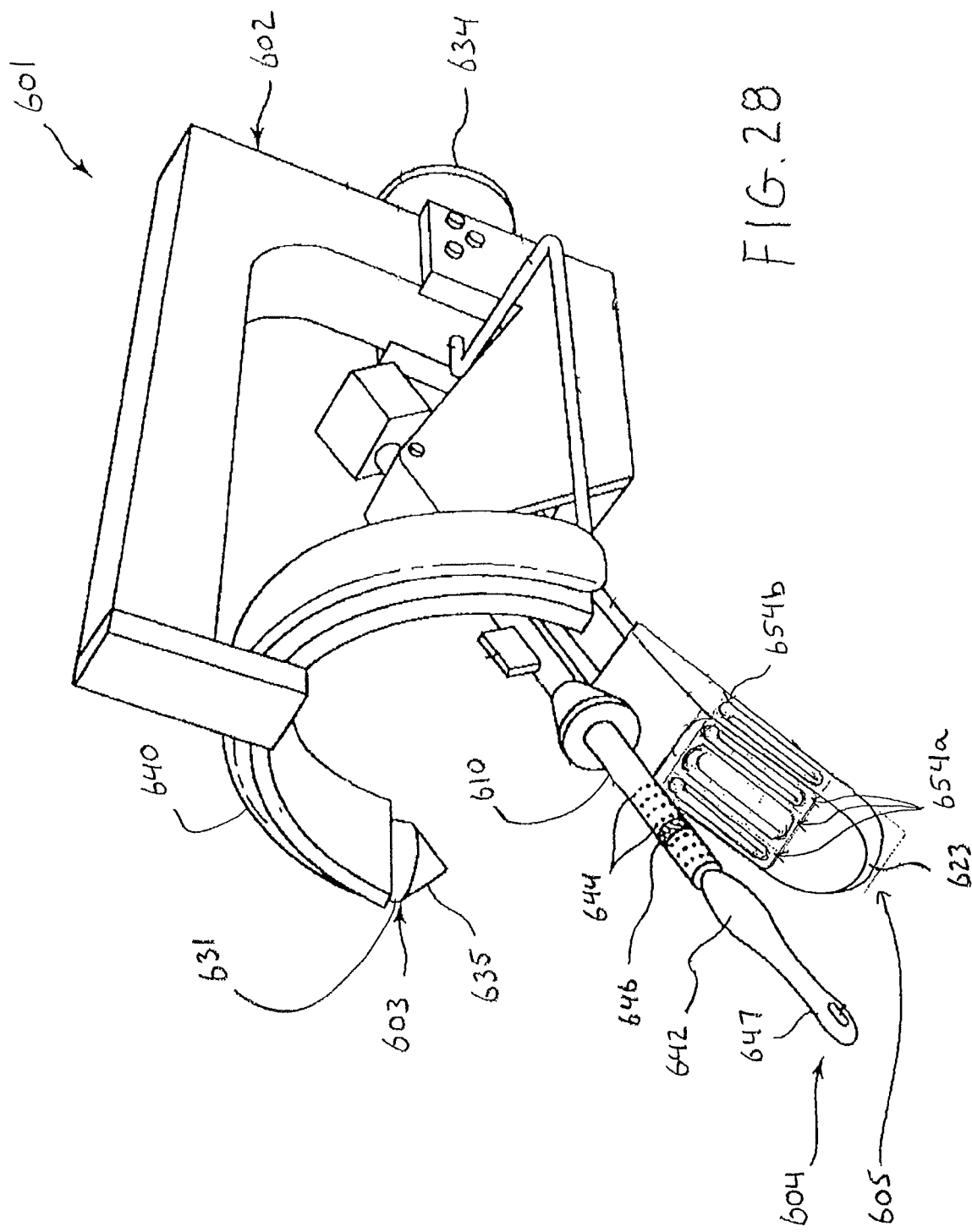
FIG. 28 is a perspective view of another embodiment of the puncture apparatus.

FIGS. 28 and 29 illustrate another different embodiment of the puncture apparatus. Details and aspects of this embodiment of the puncture apparatus that are the same as or similar to those described above in connection with the other embodiments are not be described again in detail here.

The puncture apparatus 601 shown in FIGS. 28 and 29 includes a supporting member 602, a puncture member 603, a urethral-insertion member 604 and a vaginal-insertion member 605. The urethral-insertion member 604 and the vaginal-insertion member 605 are both supported on, or mounted on, the supporting member 602. The puncture member 603 includes a puncture needle 631 possessing a sharp needle tip 635. In this embodiment, the puncture member 603 is movably positioned within a needle guide 640. The puncture member 603 moves along the predetermined orbit as described above through operation of the grasping unit or operating unit 634. That is, the grasping unit or operating unit 634 is operatively connected to the puncture member 603 so that operation of the grasping unit or operating unit 634 causes the puncture member 603 to rotate about its rotation axis and move along the predetermined orbit as described above.

The urethral-insertion member 604 is sized and configured to be inserted into and positioned in the urethra. The urethral-insertion member 604 includes an elongated tubular member 610 in which is movably positioned a balloon catheter having an inflatable balloon 642 at its distal end. The balloon 642 is similar to the balloon 111 described above. The urethral-insertion member 604 also includes a marker 61 similar to the marker 41 described above.

In this embodiment of the puncture apparatus, the urethral-insertion member 604 and the vaginal-insertion member 605 are configured to include vacuum areas or suction areas that draw a portion of the urethra wall and vaginal wall toward, and preferably into direct contact with, the outer surface of the urethral-insertion member 604 and the vaginal-insertion member 605 respectively. The tubular member 610, forming a part of the urethral-insertion member 604, includes a plurality of openings or open areas 644 passing through the tubular member 610 and communicating with the interior of the tubular member 610. The openings or open areas 644 define the vacuum area or suction area of the urethral-insertion member 604. The interior of the tubular member 610 communicates with a suction port 633 that is configured to be connected to a source of suction. As will be described in more detail below, the source of suction is operated when the urethral-insertion member 604 is positioned in the urethra, and this creates a vacuum (suction) in the vacuum area defined by the openings or open areas 644. The vacuum or suction draws the wall of the urethra towards, and preferably into direct contact with, the outer surface of the ureteral-insertion member 604.

The vaginal-insertion member 605 is sized and configured to be inserted into and positioned in the vagina. The vaginal-insertion member 605 is a generally elongated member, having a somewhat rounded forward end 623. The top surface of the vaginal-insertion member 605 includes a vacuum area (suction area) defined by a plurality of openings or open areas 654a, and both side surfaces of the vaginal-insertion member 605 include respective vacuum areas (suction areas) defined by a plurality of openings or open areas 654b. The openings or open areas 654a, 654b are in fluid communication with a suction port 643 which is connectable to a source of suction. As will be described in more detail below, the source of suction is operated when the vaginal-insertion member 605 is positioned in the vagina, and this creates a vacuum (suction) in the vacuum areas defined by the openings or open areas 654a, 654b. The vacuum or suction created at the vacuum area defined by the openings or open areas 654 draws the vaginal wall towards, preferably into direct contact with, the outer surface of the vaginal-insertion member 605.

The operating procedure using the puncture apparatus 601 is similar to the procedure described above. Initially, the puncture apparatus 601 is attached to or mounted on the patient. This involves inserting the urethral-insertion member 604 into the urethra of the living body (patient), and concurrently inserting the vaginal-insertion member 605 into the vagina of the living body (patient). The insertion of the urethral-insertion member 604 is preferably carried out to position the marker 646 at the urethra orifice or on the front side of the urethra orifice so that the distal portion of the urethral-insertion member 604 is arranged on the front side of the bladder.

Next, the source(s) of suction connected to the suction ports 633, 643 of the urethral-insertion member 604 and the vaginal-insertion member 605 is operated to create a vacuum (produce a suction force) at the vacuum areas defined by the openings or open areas 644, 654a, 654b of the vaginal-insertion member 605 and the ureteral-insertion member 604. This vacuum force draws the vaginal wall toward the vaginal-insertion member 605 and draws the urethra wall towards the urethral-insertion member 604. The operation of the suction source(s) fixes the position of the vagina and the urethra, allowing the needle to be operated to create the through-hole between the vaginal-insertion member 605 and the urethral-insertion member 604.

During the operation of the suction source(s) (i.e., while the vacuum or suction force is being produced at the vacuum areas defined by the openings or open areas 644), the puncture needle is rotated through operation of the grasping unit 634. The needle tip thus punctures skin of the living body (patient) so that the puncture member 603 enters the body. Continued rotation of the puncture member causes the puncture member to pass the obturator foramen of the pelvis, then to pass between the urethra and the vagina, and then to pass the obturator foramen of the pelvis, and finally to exit or protrudes to outside the body in a manner similar to that described above. A through-hole is thus formed which starts from the surface of the living body (patient), passes through a portion of the body as described and reaches the body surface at a region spaced from the start region. The through hole, passing between the vaginal-insertion member 605 and the urethral-insertion member 604, provides a path for placing the implant or sling. Throughout the rotation or operation of the puncture needle, the suction source(s) connected to the suction ports 633, 643 of the urethral-insertion member 604 and the vaginal-insertion member 605 continues to be operated so that the vacuum force draws the vaginal wall toward the vaginal-insertion member 605 and draws the urethra wall towards the urethral-insertion member 604.

FIGS. 30-36 illustrate an example of a vaginal insertion assembly 1005 that can be used in place of the vaginal-insertion member shown in FIGS. 28 and 29. The vaginal-insertion assembly 1005 illustrated in FIGS. 30-36 can also be used in any of the other embodiments of the puncture apparatus described above and illustrated in the drawing figures.

The vaginal-insertion assembly 1005 is configured to help facilitate insertion of the vaginal-insertion assembly into a vagina, thus assisting the medical professional during use of the puncture apparatus. More specifically, it can be appreciated from FIG. 28 that the vaginal-insertion member 605 possesses a relatively broad extent (i.e., relatively large width), thus making it difficult to rather easily introduce or insert the vaginal-insertion member into the vagina. The vaginal-insertion assembly 1005 is configured to ease the insertion of the vaginal-insertion member into the vagina.

The vaginal-insertion assembly 1005 includes a vaginal-insertion member 1010 in combination with an inserter 1012. The inserter 1012 is connected to the vaginal-insertion member 1010 by virtue of the inserter 1012 being slidably mounted on the vaginal-insertion member 1010 so that the inserter 1012 is shiftable (slidably movable) from the initial position shown in FIGS. 30-32 to the position shown in FIGS. 34-36. In the initial position shown in FIGS. 30-32, the inserter 1012 protrudes or extends distally beyond the distal end of the vaginal-insertion member 1010. That is, the inserter 1012 is connected to the vaginal-insertion member 1010 so that the distal-most end portion of the inserter 1012 is located distally beyond the distal-most end portion of the vaginal-insertion member 1010 such that during insertion of the vaginal-insertion assembly 1005 into the vagina, the distal-most end portion of the inserter 1012 enters the vagina before the distal-most end portion of the vaginal-insertion member 1010 enters the vagina.

The embodiment of the vaginal-insertion assembly 1005 shown in FIGS. 30-36 includes a plate-shaped inserter (plate-shaped member) 1012 made of a relatively rigid material that maintains its shape and size, and does not deform, during insertion of the inserter 1012 into the vagina. Examples of the material for forming the outer tube 13 include metals and resins. Examples of the metals include pseudo-elastic alloys (inclusive of superelastic alloys) such as Ni—Ti alloys, shape memory alloys, stainless steels (e.g., all types of SUS, such as SUS304, SUS303, SUS316, SUS316L, SUS316J1, SUS316J1L, SUS405, SUS430, SUS434, SUS444, SUS429, SUS430F, SUS302, etc.), cobalt alloys, noble metals such as gold, platinum, etc., tungsten alloys, and carbon-containing materials (inclusive of piano wire). Examples of the resins include polymer materials such as polyolefins (e.g., polyethylene, polypropylene, polybutene, ethylene-propylene copolymers, ethylene-vinyl acetate copolymers, ionomers, or mixtures thereof), polyvinyl chloride, polyamides, polyamide elastomers, polyesters, polyester elastomers, polyurethane, polyurethane elastomers, polyimides, fluoro-resins, and mixtures of them, which may be used either singly or in combination of two or more of them. The outer tube 13 may be composed of a multi-layer tube or the like of a composite material formed from these metals and/or resins.

As illustrated in FIGS. 30 and 32, the inserter 1012 possesses a tapering shape that tapers in a narrowing manner towards the distal most end of the inserter 1012. More specifically, the width of the inserter 1012 gradually narrows or becomes smaller towards the tip end or distal end of the inserter. Stated differently, the width of the inserter gradually increases in the proximal direction. The outer dimension of the distal-most end portion of the inserter 1012 is less than the outer dimension of the distal-most end portion of the vaginal-insertion member 1010.

As mentioned, the inserter 1012 is slidably mounted on the vaginal-insertion member 1010. As a result, the vaginal-insertion member 1010 and the inserter 1012 are movable relative to each other to reduce the distance between the distal-most end of the inserter 1012 and the distal-most end of the vaginal-insertion member 1010 after inserting the vaginal insertion assembly 1005 into the vagina so that the vaginal-insertion member 1010 is advanced forward into the vagina after the vaginal-insertion assembly is initially positioned in the vagina.

As illustrated in FIG. 31, the inserter 1012 is slidably mounted on the bottom surface of the vaginal-insertion member that is the devoid of the vacuum areas 1014. The inserter 1012 thus does not interfere with the vacuum areas 1014.

The inserter 1012 is slidably mounted on the vaginal-insertion member 1010 in any appropriate known manner. For example, the bottom surface of the vaginal-insertion member 1010 can be provided with groove-defining flanges in which the inserter 1012 is slidably positioned. Alternatively, the inserter 1012 can be outfitted with flanges or projections that engage respective grooves in the vaginal-insertion member 1010 to permit sliding movement of the inserter 1012 relative to the vaginal-insertion member.

The vaginal-insertion member 1010 includes a stopper or locking portion 1016 as generally illustrated in FIG. 32A. This stopper or locking portion 1016 includes a through slot 1030 in the inserter 1012 and a projection 1032 fixed to the vaginal-insertion member 1010. The projection 1032 projects away from the rear surface of the vaginal-insertion member 1010 and is positioned in the slot 1030. A cap 1034, having outer dimensions larger than the cross-section of the projection 1032, is connected to and overlies the projection 1032, and is positioned on the side of the inserter 1012 facing away from the vaginal-insertion member 1010. The enlarged cap 1034 prevents the inserter 1012 from being separated from the vaginal-insertion member 1010.

The slot 1030 includes a reduced-width portion 1030'. This reduced-width portion 1030' is made of a relatively soft or compliant material that deforms when sufficient force is applied. The width of the projection 1032 is greater than the width of the reduced-width portion 1030' of the slot 1030. When the inserter 1012 is in the extended or initial position shown in FIGS. 32 and 32A, the projection 1302 is positioned as shown in FIGS. 32 and 32A so that the projection is on the right side of the reduced-width portion 1030'. In this position, because the width of the projection 1302 is greater than the width of the reduced-width portion 1030' of the slot 1030, the inserter 1012 is prevented from slidably moving toward the right in FIGS. 32 and 32A in the absence of an applied force greater than a predetermined level. The stopper or locking portion 1016 thus maintains the inserter 1012 in the extended position shown in FIG. 32. The locking portion or stopper 1016 prevents relative movement between the inserter 1012 and the vaginal-insertion member 1010 until a force exceeding the predetermined amount or level is applied to the inserter 1012 in a direction urging the distal-most end of the inserter 1012 and the distal-most end of the vaginal-insertion member 1010 towards one another. That is, the locking portion or stopper 1016 maintains the vaginal-insertion member 1010 and the inserter 1012 in the relative positions shown in FIGS. 30-32 until a rearwardly directed force (i.e., a force to the right in FIGS. 30-32) exceeding the predetermined amount is applied to the inserter 1012. The locking portion or stopper 1016 thus serves as an initial position maintaining mechanism or structure that maintains the inserter 1012 in the initial position shown in FIGS. 30-32 relative to the vaginal-insertion member 1010.

During initial insertion of the vaginal-insertion assembly 1005 into the vagina, the inserter 1012 is fully extended in the forward direction as shown in FIGS. 30-32 and is locked or fixed in place relative to the vaginal-insertion member 1010 by virtue of the locking portion or stopper 1016. This initial position is illustrated in FIGS. 30-32. Once the vaginal-insertion assembly 1005 is positioned in the vagina as illustrated in FIG. 33 and moved forwardly, a force greater or higher than a predetermined level is applied to the inserter 1012, and this force is sufficiently high to overcome the restriction provided by the locking portion or stopper 1016 (reduced-width portion 1030') so that the inserter 1012 and the vaginal-insertion member 1010 move relative to one another. The force applied to the inserter 1012 can be by virtue of the tip end or distal-most end of the inserter 1012 contacting the vaginal wall. When sufficient force is applied to the inserter 1012, the projection 1032 begins to move axially over the reduced-width portion 1030' to deform the reduced-width portion 1030' of the slot in the inserter 1012. Eventually, the projection 1032 moves past the projection 1032 as shown in FIG. 32B.

The presence of the inserter 1012 with its tapering width or outer shape helps facilitate the operator's insertion of the vaginal-insertion member 1005 into the vagina. During use, the inserter 1012 is initially positioned relative to the vaginal-insertion member 1010 in the position shown in FIGS. 30-32. In this initial position, the distance (measured along the longitudinal extent of the vaginal-insertion assembly 1005) between the distal-most end (tip end) of the inserter 1012 and the distal-most end (tip end) of the vaginal-insertion member 1010 is the greatest. The inserter is then inserted through the vaginal opening 1021 of the vagina 1020 so that the distal-most end portion of the inserter 1012 is introduced into and enters the vagina. The forward movement of the vaginal-insertion assembly 1005 is continued, and then the distal-most end of the inserter 1012 contacts the internal vaginal wall as shown in FIG. 33. At this point, as the vaginal-insertion assembly 1005 continues to be pushed in the forward direction, a force is applied to the inserter 1012 that overcomes the locking force or initial position maintaining force associated with the locking portion or stopper 1016. Relative movement then occurs between the inserter 1012 and the vaginal-insertion member 1010. That is, the inserter 1012 slides relative to the vaginal-insertion member 1010 in the rearward or proximal direction (to the right in FIGS. 30-32) as indicated by the arrow in FIG. 35. This thus allows the vaginal insertion member 1010 to be moved further into the vagina, and relative to the inserter 1012, so that the vacuum areas 1014 are positioned inside the vagina at the desired location for proper affect and operation as described above.

Figure 37:
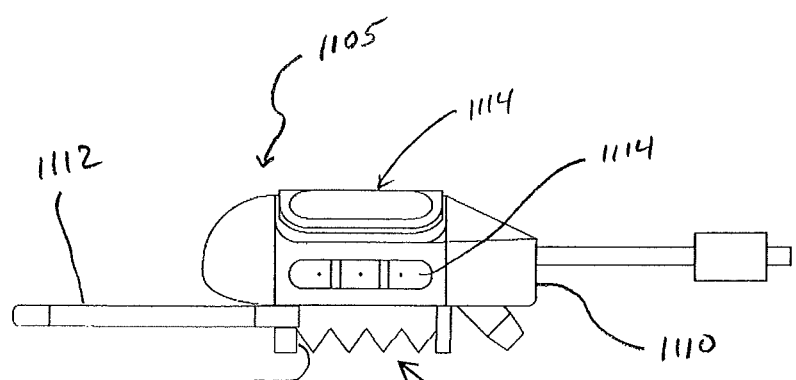
FIG. 37 is a side view of a vaginal-insertion assembly according to another embodiment disclosed by way of example.
Figure 38:
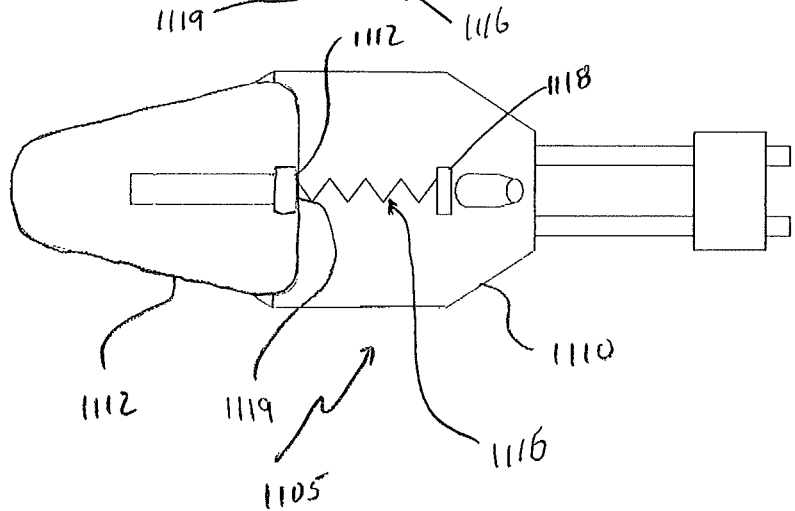
FIG. 38 is a bottom view of the vaginal-insertion assembly shown in FIG. 37.

FIGS. 37 and 38 illustrate another embodiment of the vaginal-insertion assembly 1105 that can be used in place of, or as a specific form of, the vaginal-insertion member in the puncture apparatus illustrated in FIGS. 28 and 29. The vaginal-insertion assembly 1105 can also be used together with any of the other embodiments of the puncture apparatus described above and illustrated in the drawing figures.

This embodiment of the vaginal-insertion assembly 1105 is the same as the embodiment shown in FIGS. 30-36 in that the assembly includes a vaginal-insertion member 1110 and an inserter 1112 slidably mounted on the bottom surface of the vaginal-insertion member 1110. The difference between this embodiment of the vaginal-insertion assembly 1105 shown in FIGS. 37 and 38 relative to the embodiment shown in FIGS. 30-36 is the mechanism or structure that maintains the inserter 1112 in the initial extended position relative to the vaginal-insertion member 1110 until a force above the predetermined level is applied to the inserter 1112. In this embodiment shown in FIGS. 36 and 37, the initial position maintaining mechanism or structure is a spring 1116. In this illustrated example, the spring 1116 is a compression spring. One end of the spring 1116 is connected to or acts on a portion 1118 of the vaginal-insertion member 1110 while the opposite end of the spring is connected to or acts on a portion 1119 of the inserter 1112. The spring 1116 applies a spring force urging the inserter 1112 in the forward direction relative to the vaginal-insertion member 1110. The spring 1116 is thus configured to telescopically and longitudinally connect the inserter 1112 and the vaginal-insertion member 1110. The spring 1116 maintains the inserter 1112 and the vaginal-insertion member 1110 in the relative position shown in FIGS. 37 and 38 until a force higher than or greater than the predetermined level is applied to the inserter 1112 to urge the inserter 1112 in the proximal direction (i.e., to the right in FIGS. 37 and 38).

All other features of the vaginal-insertion assembly 1105 are similar to those described above with respect to the embodiment shown in FIGS. 30-36 and so a detailed description of such aspects of the vaginal-insertion member 1110 is not repeated here.

The inserter 1112 with its tapering outer shape or width helps facilitate the operator's insertion of the vaginal-insertion member 1110 into the vagina. During use, the inserter 1112 is initially positioned relative to the vaginal-insertion member 1110 in the position shown in FIGS. 37 and 38. In this initial position, the distance (measured along the longitudinal extent of the vaginal-insertion assembly 1105) between the distal-most end (tip end) of the inserter 1112 and the distal-most end (tip end) of the vaginal-insertion member 1110 is the greatest. The inserter 1112 is then inserted through the vaginal opening of the vagina so that the distal-most end portion of the inserter 1112 is introduced into and enters the vagina. The forward movement of the vaginal-insertion assembly 1105 continues, and then the distal-most end of the inserter 1112 encounters resistance that applies a force to the inserter 1112. This resistance encountered by the inserter can be as a result of the tip end or distal-most end of the inserter contacting the internal vaginal wall. As the vaginal-insertion assembly 1105 continues to be pushed in the forward direction, a force is applied to the inserter 1112 that overcomes the initial position maintaining force of the spring 1116. Relative movement then occurs between the inserter 1112 and the vaginal-insertion member 1110, and the inserter 1112 slides relative to the vaginal-insertion member 1110 in the rearward or proximal direction (to the right in FIGS. 37 and 38). The vaginal insertion member 1110 thus moves further into the vagina, and relative to the inserter 1112, so that the vacuum areas of the vaginal-insertion member 1110 are positioned inside the vagina at the desired location for proper affect and operation as described above.

Figure 39:
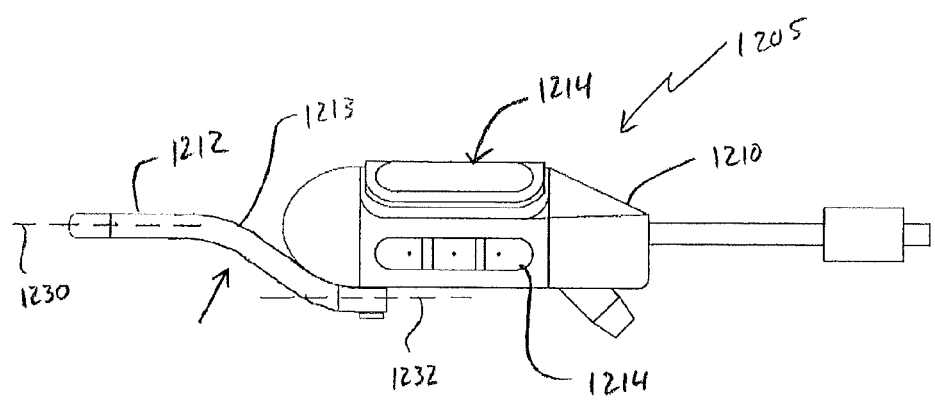
FIG. 39 is a side view of another embodiment of a vaginal-insertion assembly representing another example disclosed here before insertion into the vagina.
Figure 40:
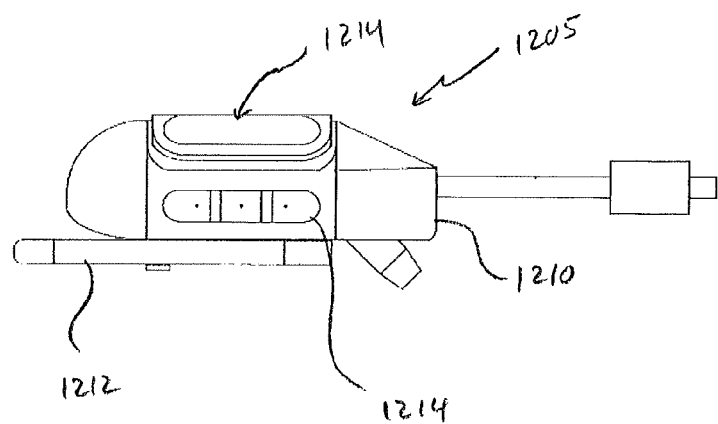
FIG. 40 is a side view of the vaginal-insertion assembly shown in FIG. 39 after insertion into the vagina.

FIGS. 39 and 40 illustrate another embodiment of the vaginal-insertion assembly disclosed by way of example. The vaginal-insertion assembly 1205 can be used in place of, or as a specific form of, the vaginal-insertion member in the puncture apparatus illustrated in FIGS. 28 and 29, and can also be used together with any of the other embodiments of the puncture apparatus described above and illustrated in the drawing figures.

This version of the vaginal-insertion assembly 1205 is similar to the embodiment shown in FIGS. 30-36, except that at least a portion of the plate-shaped inserter 1212 in this embodiment is flexible. In the illustrated embodiment, an intermediate portion 1213 of the inserter 1212 is made of flexible material. This intermediate portion of flexible material is more flexible than the portions of the inserter 1212 on the proximal and distal ends (i.e., the right and left ends in FIGS. 39 and 40) of the intermediate portion 1213. In the initial position illustrated in the FIG. 39, the central axis of the distal-most end portion of the inserter 1212 is coaxial with the axis of the vaginal-insertion member 1210, and the proximal-most end portion of the inserter 1212 is positioned under the vaginal-insertion member 1210 in facing relation to the bottom surface of the vaginal-insertion member 1210. The flexible or deformable intermediate portion 1213 can contribute to positioning the distal-most end portion of the inserter 1212 so that this coaxial relationship between the axes 1230, 1232 exists. In the initial position shown in FIG. 39, the central axis of the proximal-most end portion (right-most end portion in FIG. 39) of the inserter 1212 is parallel to and separated from (i.e., not coaxial with) the central axis of the distal-most end portion (left-most end portion in FIG. 39) of the inserter 1212. The flexible portion of the inserter 1212 serves as an initial position maintaining mechanism or structure that maintains the inserter 1212 in the extended position shown in FIG. 39. The flexible portion of the inserter, though flexible, nevertheless possesses sufficient rigidity that it can maintain the initial position shown in FIG. 39. If the inserter 1212 is moved in the distal/forward direction from the retracted position shown in FIG. 40, the inserter 1212 automatically possesses the bent/curved configuration shown in FIG. 39.

The inserter 1212 possesses a tapering shape that tapers in a narrowing manner towards the distal most end of the inserter 1212. That is, the width of the inserter 1212 gradually narrows or becomes smaller towards the tip end or distal end of the inserter. Stated differently, the width of the inserter 1212 gradually increases in the proximal direction. In addition, the outer dimension (width) of the distal-most end portion of the inserter 1212 is less than the outer dimension of the distal-most end portion of the vaginal-insertion member 1210.

The tapering outer shape or width of the inserter 1212 helps facilitate the operator's insertion of the vaginal-insertion member 1205 into the vagina. During use, the inserter 1212 is initially positioned relative to the vaginal-insertion member 1210 in the position shown in FIG. 39. In this initial position, the distance (measured along the longitudinal extent of the vaginal-insertion assembly 1205) between the distal-most end (tip end) of the inserter 1212 and the distal-most end (tip end) of the vaginal-insertion member 1210 is the greatest. The inserter 1212 is then inserted through the vaginal opening of the vagina so that the distal-most end portion of the inserter 1212 is introduced into and enters the vagina. The forward movement of the vaginal-insertion assembly 1205 continues, and then the distal-most end of the inserter 1212 encounters resistance, for example through contact with the internal vaginal wall. As the vaginal-insertion assembly 1205 continues to be moved forwardly, a force is applied to the inserter 1212 due to the resistance (e.g., contact with the vaginal wall), and this force overcomes the initial position maintaining force associated with the flexible intermediate portion 1213 of the inserter 1212. Relative movement then occurs between the inserter 1212 and the vaginal-insertion member 1210, and the inserter 1212 slides relative to the vaginal-insertion member 1210 in the rearward or proximal direction (to the right in FIGS. 39 and 40). As this occurs, the somewhat curved flexible intermediate portion thus straightens out as seen from a comparison of FIGS. 39 and 40. The vaginal insertion member 1210 thus moves further into the vagina, and relative to the inserter 1212, so that the vacuum areas of the vaginal-insertion member 1210 are positioned inside the vagina at the desired location for proper affect and operation as described above.

Figure 41:
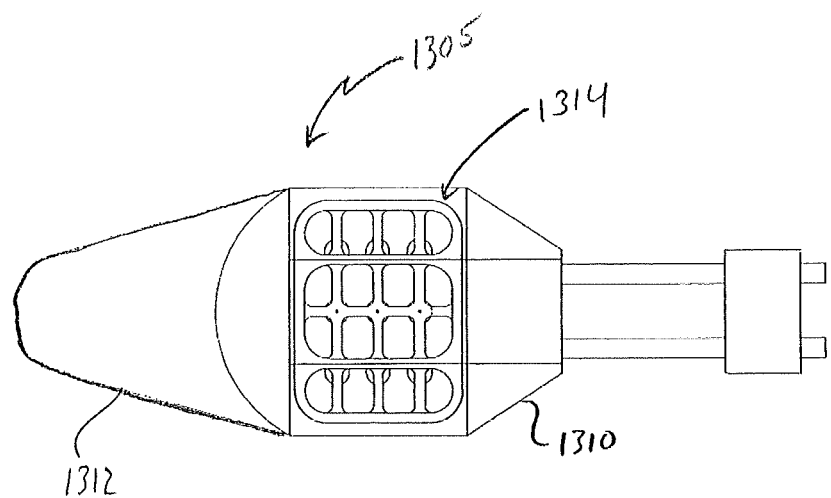
FIG. 41 is a top view of another embodiment of a vaginal-insertion assembly representing another example disclosed here before insertion into the vagina.
Figure 42:
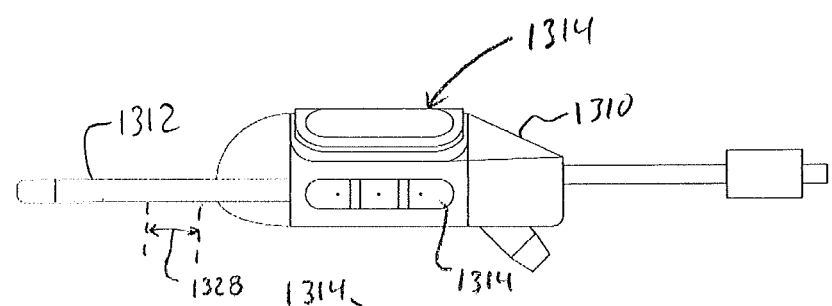
FIG. 42 is a side view of the vaginal-insertion assembly shown in FIG. 41 before insertion into the vagina.
Figure 43:
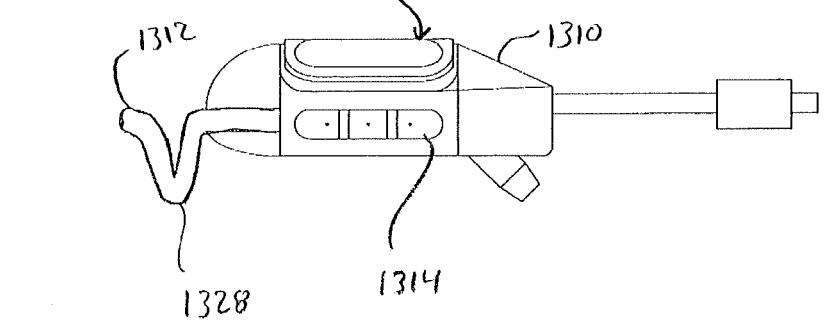
FIG. 43 is a side view of the vaginal-insertion assembly shown in FIG. 41 after insertion into the vagina.

FIGS. 41-43 illustrate another embodiment of the vaginal-insertion assembly 1305 that can be used in place of, or as a specific form of, the vaginal-insertion member 605 in the puncture apparatus illustrated in FIGS. 28 and 29. The vaginal-insertion assembly 1305 can also be used together with any of the other embodiments of the puncture apparatus described above and illustrated in the drawing figures.

This embodiment of the vaginal-insertion assembly 1305 is similar to embodiments described above in that it includes a vaginal insertion member 1310 together with an inserter 1312 that is configured to facilitate the user's insertion of the vaginal-insertion assembly into the vagina. In the embodiments described above and shown in FIGS. 30-40, the inserter is slidable relative to the vaginal-insertion member. The vaginal-insertion assembly 1305 here differs in that the inserter 1312 is not slidably mounted on the vaginal-insertion member 1310. Instead, as described below in more detail, the inserter 1312 is an elastic inserter made of elastic material.

The inserter 1312 is connected to the vaginal-insertion member 1310 so that in the initial position shown in FIGS. 41 and 42, the inserter 1312 protrudes or extends distally beyond the distal end of the vaginal-insertion member 1310. That is, the inserter 1312 is connected to the vaginal-insertion member 1310 so that the distal-most end portion of the inserter 1312 is located distally beyond the distal-most end portion of the vaginal-insertion member 1310 such that during insertion of the vaginal-insertion assembly 1305 into the vagina, the distal-most end portion of the inserter 1312 enters the vagina before the distal-most end portion of the vaginal-insertion member 1310 enters the vagina. The proximal-most end portion of the inserter 1312 is positionally fixed (i.e., cannot move) relative to the vaginal-insertion member 1310. The elastic nature of the inserter 1312 allows the inserter 1312 to be shifted from the initial extended position shown in FIG. 41 before insertion into the vagina to the deformed retracted position shown in FIG. 43 when a force above a predetermined level is applied to the inserter 1312. When the applied force above the predetermined level is removed or no longer applied to the inserter 1312, the inserter 1312 returns to the initial configuration shown in FIGS. 41 and 42.

As illustrated in FIG. 41, the inserter 1312 possesses a tapering shape that tapers in a narrowing manner towards the distal most end of the inserter 1312. That is, the width of the inserter 1312 gradually narrows or becomes smaller towards the tip end or distal end of the inserter. Stated differently, the width of the inserter gradually increases in the proximal direction. The outer dimension of the distal-most end portion of the inserter 1312 is less than the outer dimension of the distal-most end portion of the vaginal-insertion member 1310.

The inserter is a plate-shaped member made entirely or partially of elastic material allowing the inserter 1312, or a portion of the inserter 1312, to deform. The material forming the inserter 1312 can be materials like those described above for the inserter 1012. In the illustrated embodiment, the inserter 1312 is configured so that an intermediate portion 1328 of the inserter 1312 is made of elastic material.

As in the other embodiments, the inserter 1312 is positioned at the distal end of the vaginal-insertion member so that the distal-most end of the inserter 1312 is positioned distally beyond the distal-most end of the vaginal-insertion member 1310. The material forming the inserter 1312, and the dimensions of the inserter 1312, are appropriately selected so that during initial insertion of the vaginal-insertion assembly 1305 into the vagina, the vaginal-insertion assembly 1305 maintains the configuration shown in FIGS. 41 and 42, that is the inserter maintains the extended initial position shown in FIGS. 41 and 42. The inserter 1312 encounters resistance during insertion into the vagina, for example due to contact of the inserter 1312 with the vaginal wall, and so continued forward movement of the vaginal-insertion assembly 1305 results in a force being applied to the inserter 1312 in the proximal direction. When this proximally directed force applied to the inserter exceeds a predetermined level (defined by, for example, the elastic material forming the inserter or portion of the inserter, and the size/dimensions of the inserter), the inserter 1312, or a portion of the inserter 1312, deforms or collapses in the manner shown in FIG. 43. The vaginal-insertion member 1310 can thus be further inserted into the vagina and located at the desired position in the vagina.

Figure 44:
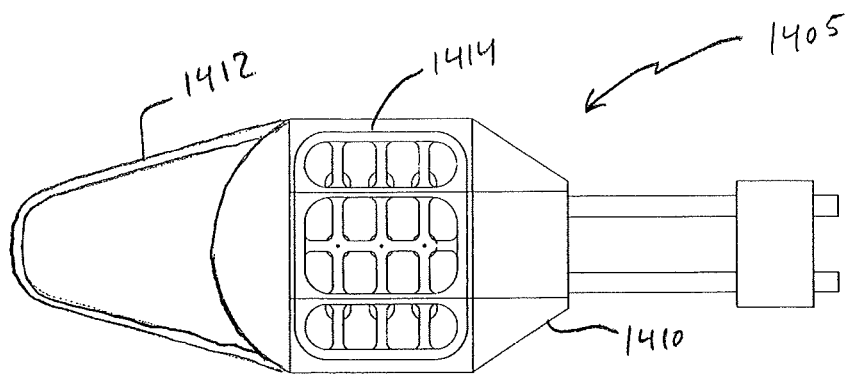
FIG. 44 is a top view of the vaginal-insertion assembly representing another example disclosed here before insertion into the vagina.
Figure 45:
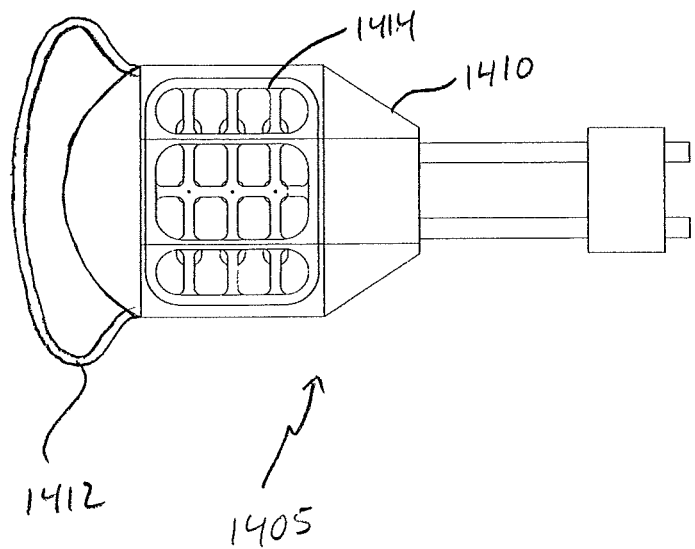
FIG. 45 is a top view of the vaginal-insertion assembly shown in FIG. 44 after insertion into the vagina.

FIGS. 44 and 45 illustrate another embodiment of the vaginal-insertion insertion assembly 1405 disclosed by way of example. This embodiment is the same as the embodiment illustrated in FIGS. 41-43, except that the inserter 1412 shown in FIGS. 44 and 45 is a wire-shaped member made of elastic material rather than a plate-shaped member. The inserter 1412 can be configured so that either a portion of the inserter 1412 is made of elastic material or so that the entirety of the inserter 1412 is made of elastic material. The elastic material allows or causes the inserter 1412 to return to its original shape shown in FIG. 44 after the force is removed.

The wire-shaped member is initially positioned in the manner shown in FIG. 44 before insertion of the vaginal-insertion assembly into the vagina. After the vaginal-insertion assembly is inserted into the vagina and moved in the forward direction, the inserter 1412 encounters resistance, for example through contact of the distal end of the wire-shaped elastic inserter 1412 with the vaginal wall, and so the wire-shaped elastic inserter 1412 deforms in the manner shown FIG. 45 so that the vaginal-insertion member 1410 can be moved further into the vagina.

The embodiments of the vaginal-insertion assembly described above and illustrated in FIGS. 30-45 help facilitate the user's use of the puncture apparatus by making it easier for the user to insert the vaginal-insertion member into the vagina through the provision of the inserter possessing the tapering shape.

Having described, by way of example, embodiments of the puncture apparatus, method, and vaginal-insertion assembly, it is to be understood that the invention here is not limited to those precise embodiments, and that various changes, modifications and equivalents can be employed by one skilled in the art without departing from the spirit or scope of the invention as defined in the claims.

What is claimed is:

1. A puncture apparatus comprising:
a supporting member;
a puncture member rotatably mounted on the supporting member to rotate about a rotation center, the puncture member possessing a distal end portion, at least a portion of the rotatable puncture member being bent or curved, the distal end portion of the puncture member constituting a needle tip which rotates together with the puncture member and is configured to puncture living body tissue as the puncture member is rotated about the rotation center;
a vaginal-insertion assembly mounted on the supporting member and positionable in a vagina to assist in properly locating the puncture member, the vaginal-insertion assembly comprising a vaginal-insertion member and an inserter connected to the vaginal-insertion member;
the inserter possessing a distal-most end portion, and the vaginal-insertion member possessing a distal-most end portion;
the inserter being connected to the vaginal-insertion member so that the distal-most end portion of the inserter is located distally beyond the distal-most end portion of the vaginal-insertion member such that during insertion of the vaginal-insertion assembly into the vagina the distal-most end portion of the inserter enters the vagina before the distal-most end portion of the vaginal-insertion member enters the vagina;
the distal-most end portion of the inserter possessing an outer dimension, and the distal-most end portion of the vaginal-insertion member possessing an outer dimension, the outer dimension of the distal-most end portion of the inserter being less than the outer dimension of the distal-most end portion of the vaginal-insertion member; and
the vaginal-insertion member and the inserter being movable relative to each other to reduce a distance between a distal-most end of the inserter and a distal-most end of the vaginal-insertion member after inserting the vaginal insertion assembly into the vagina so that the vaginal-insertion member is advanced forward into the vagina after the vaginal-insertion assembly is initially positioned in the vagina.

2. The puncture apparatus according to claim 1, wherein the inserter is a plate-shaped inserter made of a rigid material that maintains its shape and size, and does not deform, during insertion of the inserter into the vagina.

3. The puncture apparatus according to claim 1, wherein at least the distal-most end portion of the inserter possesses a width that gradually decreases toward the distal-most end of the inserter.

4. The puncture apparatus according to claim 1, wherein the inserter is slidably mounted on the vaginal-insertion member so that the distal-most end portion of the inserter is movable relative to the vaginal-insertion member by virtue of the inserting sliding relative to the vaginal-insertion member.

5. The puncture apparatus according to claim 1, wherein the vaginal-insertion member comprises a vacuum area in fluid communication with a suction port that is connectable to a source of suction, and the inserter is connected to the vaginal-insertion member at a position other than the vacuum area so that when the vaginal-insertion member and the distal-most end portion of the inserter are moved relative to one another the vacuum area is not covered by the inserter.

6. A vaginal-insertion assembly comprising:
a vaginal-insertion member possessing a distal-most end portion;
an inserter connected to the vaginal-insertion member and possessing a distal-most end portion;
the inserter being connected to the vaginal-insertion member so that the distal-most end portion of the inserter is located distally beyond the distal-most end portion of the vaginal-insertion member such that during insertion of the vaginal-insertion assembly into the vagina the distal-most end portion of the inserter enters the vagina before the distal-most end portion of the vaginal-insertion member enters the vagina;

the distal-most end portion of the inserter possessing an outer dimension, and the distal-most end portion of the vaginal-insertion member possessing an outer dimension, the outer dimension of the distal-most end portion of the inserter being less than the outer dimension of the distal-most end portion of the vaginal-insertion member; and the vaginal-insertion member and the distal-most end portion of the inserter being movable relative to each other to reduce a distance between a distal-most end of the inserter and a distal-most end of the vaginal-insertion member after inserting the vaginal insertion assembly into the vagina so that the vaginal-insertion member is advanced forward into the vagina after the vaginal-insertion assembly is initially positioned in the vagina.

7. The vaginal-insertion assembly according to claim 6, wherein the inserter is a plate-shaped inserter made of a rigid material that maintains its shape and size, and does not deform, during insertion of the inserter into the vagina.

8. The vaginal-insertion assembly according to claim 6, wherein at least the distal-most end portion of the inserter possesses a width that gradually decreases toward the distal-most end of the inserter.

9. The vaginal-insertion assembly according to claim 6, wherein the inserter is slidably mounted on the vaginal-insertion member so that the distal-most end portion of the inserter is movable relative to the vaginal-insertion member by virtue of the inserting sliding relative to the vaginal-insertion member.

10. The vaginal-insertion assembly according to claim 6, wherein the vaginal-insertion member comprises a vacuum area in fluid communication with a suction port that is connectable to a source of suction, and the inserter is connected to the vaginal-insertion member at a position other than the vacuum area so that when the inserter and the vaginal-insertion member are moved relative to one another the vacuum area is not covered by the inserter.

11. The vaginal-insertion assembly according to claim 6, further comprising a stopper positioned between the inserter and the vaginal-insertion member to prevent relative movement between the inserter and the vaginal-insertion member until a force above a predetermined level is applied in a direction urging the distal-most end of the inserter and the distal-most end of the vaginal-insertion member towards one another.

12. The vaginal-insertion assembly according to claim 11, wherein the inserter and the vaginal-insertion member are relatively slidably movable, and the inserter and the vaginal-insertion member slide relative to one another when the force is above the predetermined level.

13. The vaginal-insertion assembly according to claim 6, further comprising a spring acting between the inserter and the vaginal-insertion member, the spring applying a spring force preventing relative movement between the inserter and the vaginal-insertion member until a force above a predetermined level is applied in a direction urging the distal-most end of the inserter and the distal-most end of the vaginal-insertion member towards one another.

14. The vaginal-insertion assembly according to claim 13, wherein the inserter and the vaginal-insertion member are relatively slidably movable, and the inserter and the vaginal-insertion member slide relative to one another in opposition to the spring force when the force applied in the direction urging the distal-most end of the inserter and the distal-most end of the vaginal-insertion member towards one another is above the predetermined level.

15. The vaginal-insertion assembly according to claim 6, wherein the inserter is a plate-shaped inserter, at least a part of the plate-shaped member is a flexible portion permitting bending of the flexible portion of the plate-shaped member relative to another portion of the inserter.

16. The vaginal-insertion assembly according to claim 15, wherein the distal-most end portion of the inserter possesses a central axis that is coaxial with a central axis of the vaginal-insertion member during initial insertion of the vaginal-insertion assembly into the vagina, the flexible portion permitting the distal-most end portion of the inserter to be shifted to a position in which the central axis of the distal-most end portion of the inserter is not coaxial with the central axis of the vaginal-insertion member when the inserter and the vaginal-insertion member are moved relative to one another.

17. The vaginal-insertion assembly according to claim 6, wherein the inserter is a deformable elastic member which begins to deform when a force above a predetermined level is applied in a direction urging the distal-most end of the inserter and the distal-most end of the vaginal-insertion member towards one another.

18. The vaginal-insertion assembly according to claim 17, wherein the inserter is a deformable plate-shaped elastic member.

19. The vaginal-insertion assembly according to claim 17, wherein the inserter is a deformable wire-shaped elastic member.

20. A method of forming a path in living body tissue comprising:

inserting a vaginal-insertion assembly into a vagina of a living body, the vaginal-insertion assembly being mounted on a support frame and including a vaginal-insertion member and an inserter, the inserter being connected to the vaginal-insertion member;

the insertion of the vaginal-insertion assembly into the vagina of the living body including inserting a distal-most end portion of the inserter into the vagina before inserting a distal-most end portion of the vaginal-insertion member into the vagina, the distal-most end portion of the inserter possessing an outer dimension, and the distal-most end portion of the vaginal-insertion member possessing an outer dimension, the outer dimension of the distal-most end portion of the inserter being less than the outer dimension of the distal-most end portion of the vaginal-insertion member;

relatively moving the vaginal-insertion member and the distal-most end portion of the inserter while the inserter is in the vagina to reduce a distance between a distal-most end of the inserter and a distal-most end of the vaginal-insertion member and forwardly move the vaginal-insertion member into the vagina after the vaginal-insertion assembly; and rotating a puncture member which is mounted on the support frame in a rotational direction about a rotation center while the vaginal-insertion member is positioned in the vagina to puncture tissue of the living body, to move the puncture member along a path of rotational movement passing between the rotation center and the vaginal-insertion assembly, and to exit the living body.

* * * * *